United States Patent
Ghosh

(10) Patent No.: US 11,291,845 B2
(45) Date of Patent: Apr. 5, 2022

(54) MEDICAL DEVICE SYSTEM AND METHOD FOR DETERMINING HIS BUNDLE PACING CAPTURE

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 60 days.

(21) Appl. No.: 16/791,661

(22) Filed: Feb. 14, 2020

(65) Prior Publication Data

US 2020/0261731 A1 Aug. 20, 2020

Related U.S. Application Data

(60) Provisional application No. 62/807,109, filed on Feb. 18, 2019.

(51) Int. Cl.
| | |
|---|---|
| *A61N 1/37* | (2006.01) |
| *A61N 1/365* | (2006.01) |
| *A61N 1/372* | (2006.01) |
| *A61N 1/39* | (2006.01) |

(52) U.S. Cl.
CPC ....... *A61N 1/3704* (2013.01); *A61N 1/36507* (2013.01); *A61N 1/3712* (2013.01); *A61N 1/37223* (2013.01); *A61N 1/39622* (2017.08)

(58) Field of Classification Search
None
See application file for complete search history.

(56) References Cited

U.S. PATENT DOCUMENTS

| | | | |
|---|---|---|---|
| 8,565,880 B2 | 10/2013 | Dong et al. | |
| 8,738,132 B1 | 5/2014 | Ghosh et al. | |
| 8,761,880 B2 | 6/2014 | Maskara et al. | |
| 8,972,228 B2 | 3/2015 | Ghosh et al. | |
| 9,168,382 B2 | 10/2015 | Shuros et al. | |
| 9,227,073 B2 | 1/2016 | Bohn et al. | |
| 9,278,218 B2 | 3/2016 | Karst et al. | |
| 9,320,446 B2 | 4/2016 | Gillberg et al. | |
| 9,486,151 B2 | 11/2016 | Ghosh et al. | |
| 9,986,928 B2 | 6/2018 | Gillberg et al. | |
| 2005/0004607 A1 | 1/2005 | Bjorling et al. | |
| 2011/0264158 A1 | 10/2011 | Dong et al. | |
| 2012/0239106 A1 | 9/2012 | Maskara et al. | |
| 2013/0158621 A1 | 6/2013 | Ding et al. | |
| 2016/0045738 A1 | 2/2016 | Ghosh et al. | |
| 2018/0263522 A1 | 9/2018 | Ghosh et al. | |
| 2019/0192860 A1* | 6/2019 | Ghosh ................ | A61N 1/36507 |

OTHER PUBLICATIONS (PCT/US2020/018503) PCT Notification of Transmittal of the International Search Report and the Written Opinion of the International Searching Authority, dated Jun. 9, 2020, 8 pages.

* cited by examiner

*Primary Examiner* — Brian T Gedeon

(57) ABSTRACT

In a medical device system, a computer apparatus is configured to receive body surface electrical signals from an electrode apparatus including multiple external electrodes. The computing apparatus generates electrical dyssynchrony data from the body surface electrical signals during delivery of His bundle pacing pulses and identifies effective His bundle capture based on the electrical dyssynchrony data. The computing apparatus generates an indication of His bundle capture in response to identifying the effective His bundle capture.

27 Claims, 10 Drawing Sheets

MEDICAL DEVICE SYSTEM AND METHOD FOR DETERMINING HIS BUNDLE PACING CAPTURE

REFERENCE TO RELATED APPLICATION

This application claims the benefit of U.S. Patent Application No. 62/807,109, filed provisionally on Feb. 18, 2019, incorporated herein by reference in its entirety.

TECHNICAL FIELD

This disclosure relates to a medical device system and method for determining capture of the His bundle and establishing a His bundle capture detection threshold.

BACKGROUND

During normal sinus rhythm (NSR), the heart beat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles.

Patients with a conduction system abnormality, e.g., poor AV node conduction or poor SA node function, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself is generally implanted in a subcutaneous pocket with the transvenous ventricular lead tunneled to the subcutaneous pocket.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and promote AV synchrony when the AV node or other conduction abnormalities are present.

Ventricular pacing at the right ventricular apex using a conventional transvenous lead for positioning endocardial electrodes in the vicinity of the right ventricular apex has been found to be associated with increased risk of atrial fibrillation and heart failure. Alternative pacing sites have been investigated or proposed, such as pacing of the His bundle. Cardiac pacing of the His bundle has been proposed to provide ventricular pacing along the heart's natural conduction system in a patient having a conduction defect higher than the His bundle, e.g., having AV conduction block. Pacing the ventricles via the His bundle allows recruitment along the heart's natural conduction system, including the Purkinje fibers, and is hypothesized to promote more physiologically normal electrical and mechanical synchrony than other pacing sites, such as the ventricular apex.

SUMMARY

The techniques of this disclosure generally relate to establishing a His bundle capture detection threshold for detecting capture of the His bundle during cardiac pacing e.g., by an implantable pacemaker configured as a His bundle pacing device. A medical device system including an electrode apparatus for sensing body surface cardiac electrical signals and a computing apparatus to receive the cardiac electrical signals is configured to determine at least one metric of electrical dyssynchrony of ventricular depolarization during His bundle pacing. Evaluation of the electrical dyssynchrony by the computing apparatus is used to verify effective His bundle capture based on a relatively low electrical dyssynchrony metric, indicating capture and conduction along the intrinsic ventricular conduction system, including both the right and left bundle branches. The His bundle pacing device is configured to deliver His bundle pacing pulses and sense cardiac electrical signals for determining a feature of the QRS waveform of the cardiac electrical signal received by the His bundle pacing device. When effective His bundle capture is verified by the computing apparatus based on the metric of ventricular dyssynchrony, the His bundle pacing device establishes the His bundle capture detection threshold based on the value of the determined feature of the QRS waveform. The His bundle pacing device, operating according to the techniques disclosed herein, delivers His bundle pacing and monitors for His bundle capture by determining the feature of the QRS waveform of the cardiac electrical signal and comparing the feature to the established His bundle capture detection threshold. The His bundle pacing device may adjust cardiac pacing control parameters to maintain capture of the His bundle based on the capture monitoring.

In one example, the disclosure provides a medical device system including an electrode apparatus having multiple external electrodes configured for monitoring body surface electrical signals of a patient and a computing apparatus coupled to the electrode apparatus. The computing apparatus includes processing circuitry and is configured to generate cardiac electrical dyssynchrony data from the body surface electrical signals received from the external electrodes during delivery of His bundle pacing pulses and identify effective His bundle capture by the His bundle pacing pulses based on the electrical dyssynchrony data. The effective His bundle capture comprises capture of both a left bundle branch and a right bundle branch of a His bundle. The computing apparatus is further configured to generate an indication of His bundle capture in response to identifying the effective His bundle capture.

In another example, the disclosure provides a method performed by a medical device system. The method includes receiving body surface electrical signals by a computing apparatus from an electrode apparatus having multiple external electrodes, generating electrical dyssynchrony data by the computing apparatus during delivery of His bundle pacing pulses and identifying effective His bundle capture based on the electrical dyssynchrony data. The method further includes generating an indication of His bundle capture by the computing apparatus in response to identifying the effective His bundle capture.

In yet another example, the disclosure provides a non-transitory, computer-readable storage medium comprising a set of instructions which, when executed by a processor of a computing apparatus, cause the computing apparatus to receive body surface electrical signals from an electrode apparatus having multiple external electrodes, generate electrical dyssynchrony data from the body surface electrical signals received from the external electrodes during delivery of His bundle pacing pulses, and identify effective His bundle capture based on the electrical dyssynchrony data.

The instructions further cause the computing apparatus to generate an indication of His bundle capture in response to identifying the effective His bundle capture.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
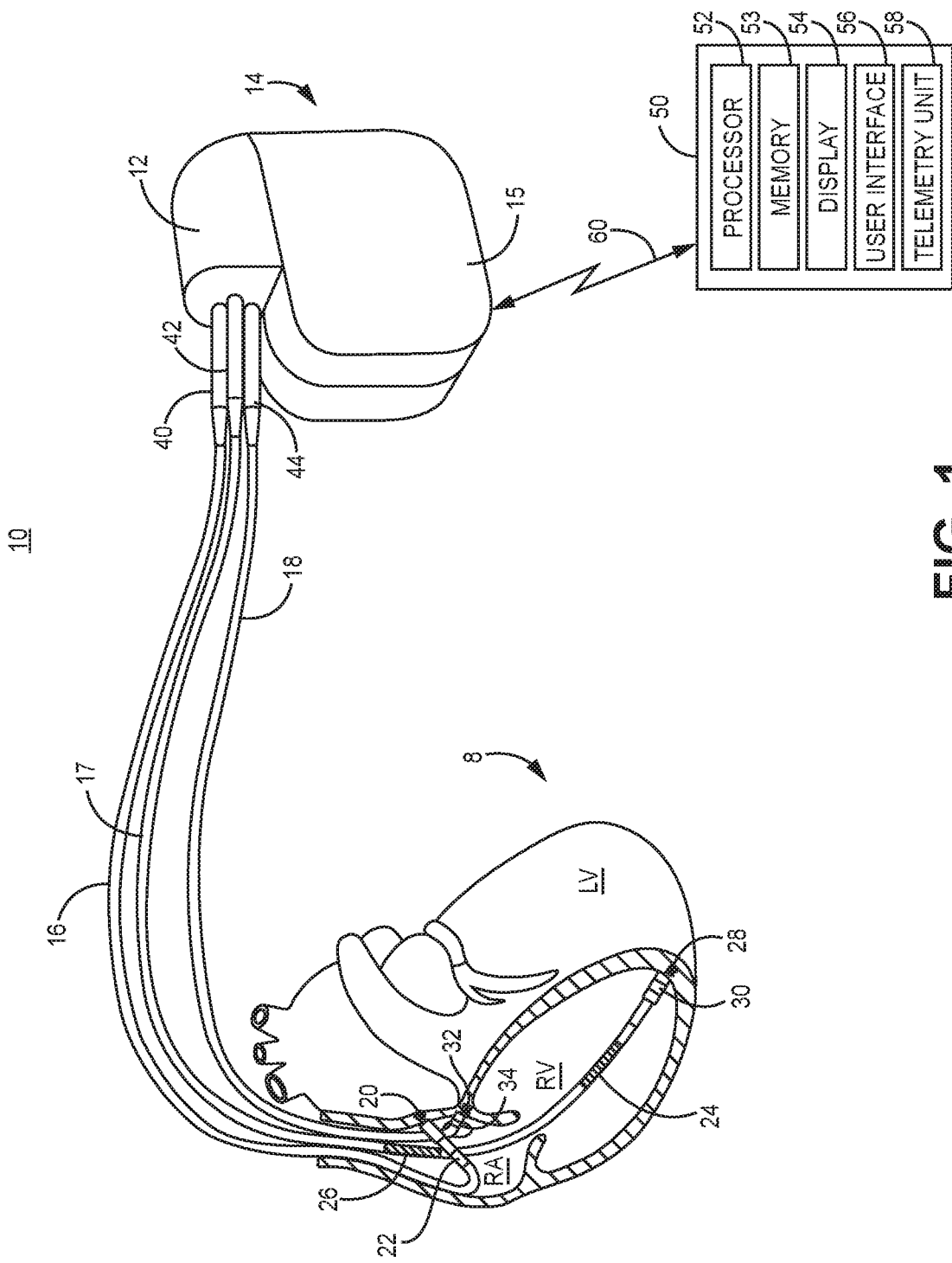
FIG. 1 is a conceptual diagram of a medical device system including a His bundle pacing device capable of pacing and sensing in a patient's heart.

A medical device system for delivering His bundle pacing and detecting and monitoring capture of the His bundle is described herein. A cardiac tissue is "captured" when an electrical pacing pulse delivers sufficient electrical energy to cause depolarization of the cardiac tissue. The depolarization of the cardiac tissue is sometimes referred to as the electrical "evoked response," and is subsequently followed by mechanical contraction of the heart chamber(s). In order to effectively capture and pace the heart to achieve a desired therapeutic effect, cardiac pacing pulses need to have a pulse energy that is equal to or greater than the capture threshold of the cardiac tissue at the pacing site. A pacing capture threshold test may be performed to determine the minimum pacing pulse voltage amplitude for a given pacing pulse width (or minimum pulse width for a given voltage amplitude) that causes an evoked response. Determination of the pacing capture threshold enables proper programming of the pacing pulse amplitude and pulse width to promote effective pacing and avoid loss of capture. Capture monitoring by the pacemaker during ongoing pacing allows automatic adjustments to the pacing pulse amplitude and/or width to maintain capture if loss of capture is detected.

Effective capture of the His bundle by a His bundle pacing pulse occurs when the His bundle is captured and the evoked depolarization is conducted via the bundle branch system to both the right and left ventricles thereby increasing the electrical synchrony of the right and left ventricles. Increased electrical synchrony (or decreased electrical dyssynchrony) of the right and left ventricles is evidenced by a narrow, or relative narrowing of, the QRS waveform width of a cardiac electrical signal. Effective His bundle capture may occur with or without capture of the ventricular myocardial tissue nearby the His bundle pacing electrodes. Ineffective His bundle capture occurs when no His bundle capture occurs or when the His bundle is partially captured resulting in conduction along a portion of the bundle branch system, e.g., only along the right bundle branch or only along the left bundle branch. Ineffective His bundle capture is evidenced by a wide QRS waveform and may occur with or without capture of nearby ventricular myocardium. In some cases, a complete loss of capture occurs, when the His bundle pacing pulse output is less than both the His bundle capture threshold and the myocardial capture threshold or an intrinsic R-wave is conducted earlier than the His bundle pacing pulse.

When pacing pulses are delivered by electrodes positioned in the heart to pace the His bundle, it is possible to capture only the His bundle tissue, capture both the His bundle and surrounding ventricular myocardium, or capture the surrounding ventricular myocardium without capturing the His bundle. Capture of only the His bundle may be referred to as "selective" His bundle (SHB) capture. Capture of the His bundle and surrounding ventricular myocardial tissue may be referred to as "non-selective" His bundle (NSHB) capture. Both SHB and NSHB capture may be effective His bundle capture since conduction along both the right and left bundle branches may occur resulting in increased electrical synchrony as evidenced by a narrow QRS waveform width. A narrow QRS waveform width is a QRS width that is less than a predefined threshold and/or less than a previously determined QRS waveform width when His bundle pacing is not being delivered. When His bundle pacing is not being delivered, a QRS waveform may occur with intrinsically conducted R-waves or with myocardial pacing of the ventricles. Under both of these conditions the QRS waveform is expected to be wider than during effective His bundle pacing.

Capture of the surrounding ventricular myocardium by a His bundle pacing pulse without capturing the His bundle is referred to herein as ventricular myocardial (VM) capture and is considered ineffective His bundle capture. In other instances, His bundle pacing is ineffective when only the right bundle branch is captured, when only the left bundle branch is captured, or when atrial capture occurs instead of the His bundle. Sometimes fusion may occur when a His bundle pacing pulse captures the His bundle and an intrinsic depolarization occurs simultaneously. These different types of effective and ineffective His bundle capture may result in variation of one or more features of the QRS waveform of the cardiac electrical signal sensed by the His bundle pacing device. As such, establishing a capture detection threshold value of a QRS waveform as sensed by the His bundle pacing device that distinguishes effective His bundle capture from ineffective His bundle capture enables the His bundle pacing device to reliably detect effective His bundle capture and provide an appropriate response when effective His bundle capture is not detected, e.g., make an adjustment to the His bundle pacing therapy.

Apparatus and techniques are disclosed herein for establishing a patient-specific capture detection threshold value applied to a feature of the QRS waveform by the His bundle pacing device by which effective His bundle capture can be reliably detected with a high degree of certainty. Reliable detection of effective His bundle capture enables the His bundle pacing device to adjust to the pacing pulse output to maintain effective His bundle capture, promoting therapeutic efficacy of the His bundle pacing. Reliable detection of effective His bundle capture may allow the pacemaker to adjust the pacing pulse amplitude to a safety margin greater than the His bundle pacing capture threshold while avoiding an unnecessarily high pulse output that increases the current drain of the pacemaker power source. It is noted that, as used herein the "His bundle pacing capture threshold" refers to the pacing pulse output or energy, e.g., corresponding to the pacing pulse voltage amplitude and pacing pulse width, that is the minimum pacing pulse output that captures the His bundle. The "His bundle capture detection threshold," on the other hand, is a value of a cardiac electrical signal feature, e.g., a QRS waveform feature such as QRS waveform width, QRS waveform area, or QRS waveform delay time following the His pacing pulse, that corresponds to effective capture of the His bundle by the pacing pulse.

FIG. 1 is a conceptual diagram of an implantable medical device (IMD) system 10 capable of pacing and sensing in a patient's heart 8. The IMD system 10 includes IMD 14 coupled to a patient's heart 8 via transvenous electrical leads 16, 17 and 18. IMD 14 is configured for His bundle pacing and is also referred to herein as a "His bundle pacing device." In the example of FIG. 1, IMD 14 is a dual chamber device capable of pacing the right atrium (RA) and pacing the ventricles via the His bundle. Housing 15 encloses internal circuitry corresponding to the various circuits and components described in conjunction with FIG. 3 below, for sensing cardiac signals from heart 8, detecting arrhythmias, controlling therapy delivery and monitoring His bundle capture using the techniques disclosed herein.

IMD 14 includes a connector block 12 that may be configured to receive the proximal ends of a RA lead 16, an optional right ventricular (RV) lead 17 and a His pacing lead 18, which are each advanced transvenously for positioning electrodes for sensing and stimulation in the RA, RV and the vicinity of the His bundle, respectively. RA lead 16 is positioned such that its distal end is in the vicinity of the right atrium and the superior vena cava. RA lead 16 is equipped with pacing and sensing electrodes 20 and 22, shown as a tip electrode 20 and a ring electrode 22 spaced proximally from tip electrode 20. The electrodes 20 and 22 provide sensing and pacing in the right atrium and are each connected to a respective insulated conductor extending within the elongated body of RA lead 16. Each insulated conductor is coupled at its proximal end to a connector carried by proximal lead connector 40.

His lead 18 is advanced within the right atrium to position electrodes 32 and 34 for pacing and sensing in the vicinity of the His bundle. His lead tip electrode 32 may be a helical electrode that is advanced into the inferior end of the interatrial septum, beneath the AV node and near the tricuspid valve annulus to position tip electrode 32 in or proximate to the His bundle. A ring electrode 34 spaced proximally from tip electrode 32 may be used as the return electrode with the cathode tip electrode 32 for pacing the right and left ventricles via the native ventricular conduction system extending from the His bundle. An intracardiac electrogram (EGM) signal may be produced by IMD 14 from the cardiac electrical signal sensed using the tip electrode 32 and ring electrode 34 of His lead 18 and received by sensing circuitry included in IMD 14. As described below, the EGM signal produced from the cardiac electrical signal received via His lead 18 may be used for detecting capture of the His bundle and discriminating from loss of His bundle capture. The electrodes 32 and 34 are coupled to respective insulated conductors extending within the elongated body of His lead 18, which provide electrical connection to the proximal lead connector 44 coupled to connector block 12.

In some examples, IMD 14 may optionally be coupled to RV lead 17 for positioning electrodes within the RV for sensing RV cardiac signals and delivering pacing or shocking pulses in the RV. For these purposes, RV lead 17 is equipped with pacing and sensing electrodes shown as a tip electrode 28 and a ring electrode 30. RV lead 17 is further shown to carry defibrillation electrodes 24 and 26, which may be elongated coil electrodes used to deliver high voltage CV/DF pulses. Defibrillation electrode 24 may be referred to as the "RV defibrillation electrode" or "RV coil electrode" because it may be carried along RV lead 17 such that it is positioned substantially within the right ventricle when distal pacing and sensing electrodes 28 and 30 are positioned for pacing and sensing in the right ventricle. Defibrillation electrode 26 may be referred to as a "superior vena cava (SVC) defibrillation electrode" or "SVC coil electrode" because it may be carried along RV lead 17 such that it is positioned at least partially along the SVC when the distal end of RV lead 17 is advanced within the right ventricle.

Each of electrodes 24, 26, 28 and 30 are connected to a respective insulated conductor extending within the body of RV lead 17. The proximal end of the insulated conductors are coupled to corresponding connectors carried by proximal lead connector 42, e.g., a DF-4 connector, for providing electrical connection to IMD 14. Housing 15 may function as an active electrode during CV/DF shock delivery in conjunction with RV coil electrode 24 or SVC coil electrode 26. In some examples, housing 15 may function as a return electrode for unipolar sensing or pacing configurations with any of the electrodes carried by leads 16, 17 and 18.

It is to be understood that although IMD 14 is illustrated in FIG. 1 as an implantable cardioverter defibrillator capable of delivering both low voltage cardiac pacing therapies and high voltage cardioversion and defibrillation (CV/DF) shocks, IMD 14 may be configured as a dual-chamber pacemaker in other examples coupled to only RA lead 16 and His lead 18 without having CV/DF shock delivery capabilities and without being coupled to a third lead, such as RV lead 17. In still other examples, IMD 14 may be a single chamber device coupled only to His lead 18 for delivering pacing pulses to the ventricles for at least maintaining a minimum ventricular rate, eliminating both the RA lead 16 and RV lead 17.

An external device 50 is shown in telemetric communication with IMD 14 by a communication link 60. External device 50 may include a processor 52, memory 53, display unit 54, user interface 56 and telemetry unit 58. Processor 52 controls external device operations and processes data and signals received from IMD 14. Display unit 54, which may include a graphical user interface, displays data and other information to a user for reviewing IMD operation and programmed parameters as well as cardiac electrical signals retrieved from IMD 14. Data obtained from IMD 14 via communication link 60 may be displayed on display 54. For example, a clinician may view cardiac electrical signals received from IMD 14 and/or results of His capture threshold testing and monitoring or data derived therefrom.

User interface 56 may include a mouse, touch screen, key pad or the like to enable a user to interact with external device 50 to initiate a telemetry session with IMD 14 for retrieving data from and/or transmitting data to IMD 14, including programmable parameters for controlling His capture determination as described herein. Telemetry unit 58 includes a transceiver and antenna configured for bidirectional communication with a telemetry circuit included in IMD 14 and is configured to operate in conjunction with processor 52 for sending and receiving data relating to IMD functions via communication link 60, which may include data relating to His bundle capture detection threshold.

Communication link 60 may be established between IMD 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes and delivered therapies, may be retrieved from IMD 14 by external device 50 following an interrogation command.

External device 50 may be embodied as a programmer used in a hospital, clinic or physician's office to retrieve data from IMD 14 and to program operating parameters and algorithms in IMD 14 for controlling IMD functions. External device 50 may alternatively be embodied as a home monitor or hand held device. External device 50 may be used to program cardiac signal sensing parameters, cardiac rhythm detection parameters and therapy control parameters used by IMD 14. As described below in conjunction with FIG. 4, external device 50 may be embodied as a computing apparatus coupled to an electrode apparatus for analyzing body surface cardiac electrical signals for identifying effective His bundle capture by IMD 14. In other examples, external device 50 is in communication with the computing apparatus of FIG. 4 for transmitting a notification of effective His bundle capture to IMD 14.

Figure 2:
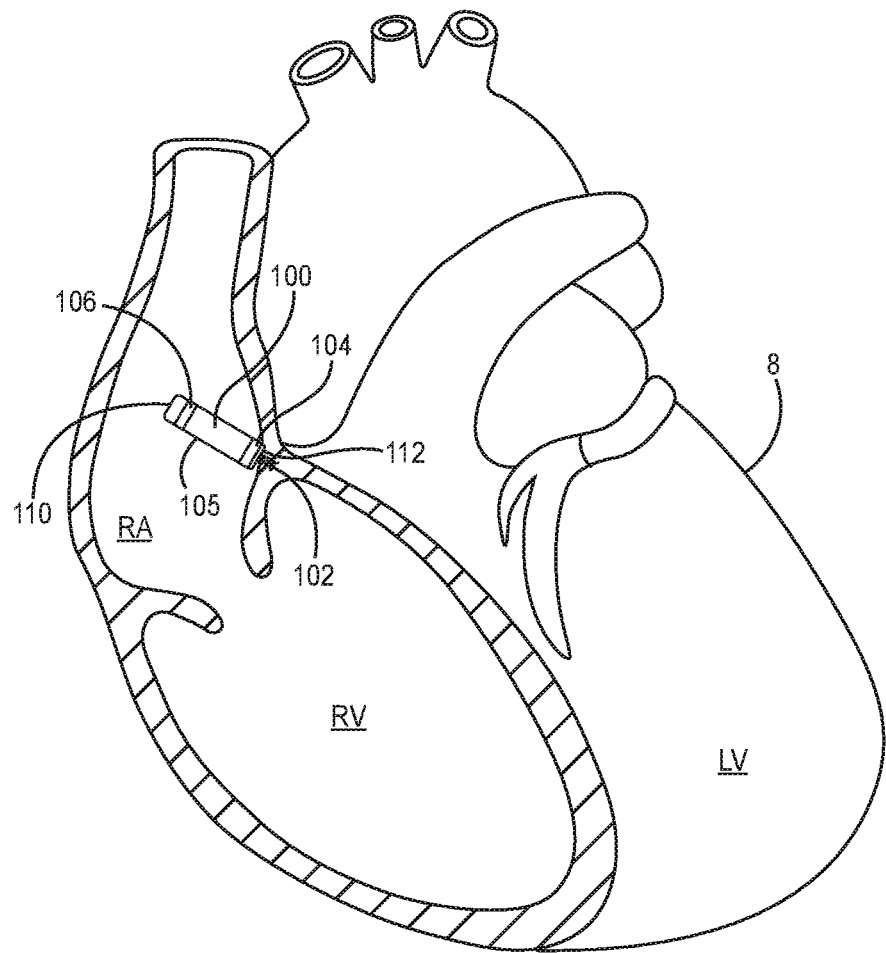
FIG. 2 is a conceptual diagram of a leadless intracardiac pacemaker configured as a His bundle pacing device.

FIG. 2 is a conceptual diagram of a leadless intracardiac pacemaker 100 configured as a His bundle pacing device. Pacemaker 100 is shown positioned within the RA for providing ventricular pacing via the His bundle. Pacemaker 100 may include a distal tip electrode 102 extending away from a distal end 112 of the pacemaker housing 105. Intracardiac pacemaker 100 is configured for implantation in the RA of the patient's heart 8 to place distal tip electrode 102 for delivering pacing pulses to the His bundle. For example, the distal tip electrode 102 may be inserted into the inferior end of the interatrial septum, beneath the AV node and near the tricuspid valve annulus to position tip electrode 102 in, along or proximate to the His bundle. Distal tip electrode 102 may be a helical electrode providing fixation to anchor the pacemaker 100 at the implant position. In other examples, pacemaker 100 may include a fixation member that includes one or more tines, hooks, barbs, helices or other fixation member(s) that anchor the distal end of the pacemaker 100 at the implant site.

A portion of the distal tip electrode 102 may be electrically insulated such that only the most distal end of tip electrode 102, furthest from housing distal end 112, is exposed to provide targeted pacing at a tissue site that includes a portion of the His bundle. One or more housing-based electrodes 104 and 106 may be carried on the surface of the housing of pacemaker 100, near or on proximal end 110 of pacemaker 100. Pacing of the His bundle may be achieved using the distal tip electrode 102 as the cathode electrode and either of the housing-based electrodes 104 and 106 as the return anode.

Cardiac electrical signals produced by heart 8 may be sensed by pacemaker 100 using a sensing electrode pair selected from electrodes 102, 104 and 106. For example, a near-field signal may be sensed using distal tip electrode 112 and proximal housing-based electrode 104. A second electrical signal, which is a relatively more far-field signal, may be sensed using electrodes 104 and 106. One or both of the near-field and the far-field cardiac electrical signals may be analyzed for determining His bundle capture and discriminating between effective His bundle capture and ineffective His bundle capture or loss of capture according to the techniques disclosed herein.

Figure 3:
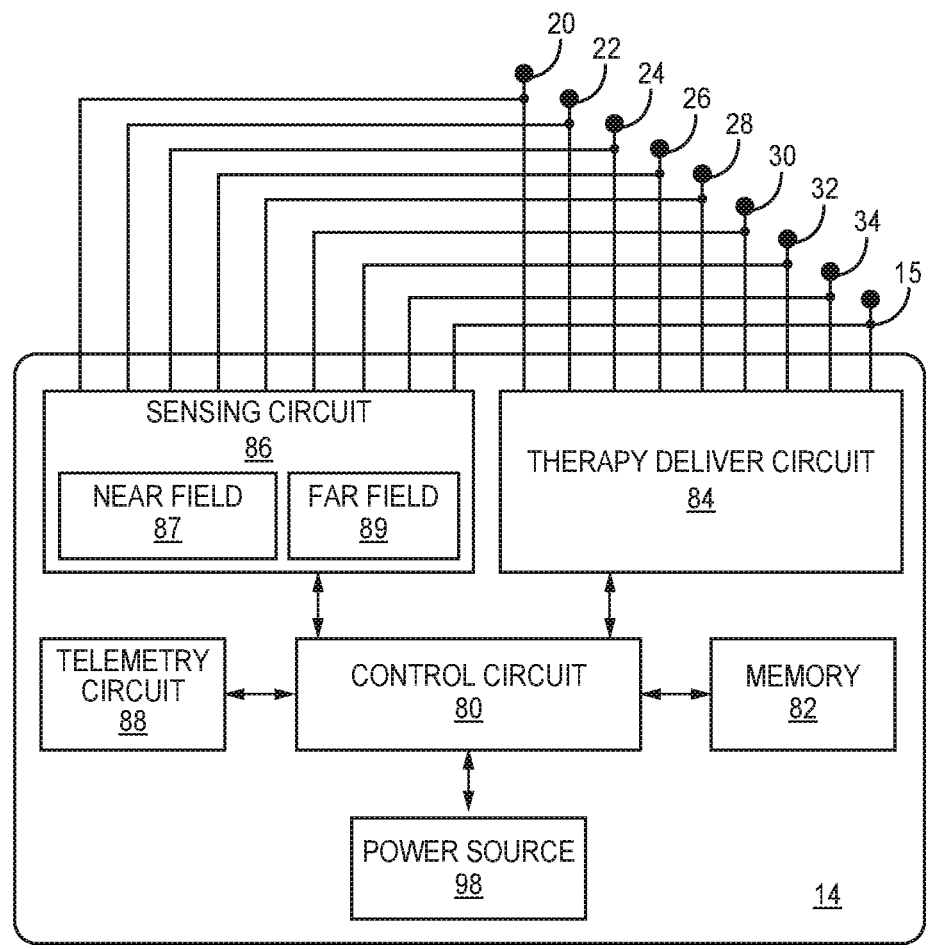
FIG. 3 is a schematic diagram of circuitry that may be enclosed within a His bundle pacing device configured to perform His bundle pacing and capture detection according to one example.

FIG. 3 is a schematic diagram of circuitry that may be enclosed within a His bundle pacing device configured to perform His bundle pacing and capture detection according to one example. The block diagram of FIG. 3 represents IMD 14 of FIG. 1 for the sake of illustration but it is to be understood that the functionality attributed to the various circuits and components shown in FIG. 3 for performing His bundle pacing and detection and discrimination of effective and ineffective His bundle capture, among other types of capture and/or loss of capture, may be similarly implemented in the intracardiac pacemaker 100 of FIG. 2 and generally relates to a His bundle pacing device capable of delivering His bundle pacing pulses, sensing cardiac electrical signals and detecting His bundle capture according to the techniques disclosed herein.

Housing 15 is represented as an electrode in FIG. 3 for use in sensing and cardiac electrical stimulation pulse delivery. The electronic circuitry enclosed within housing 15 includes software, firmware and hardware that cooperatively monitor electrical cardiac signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, telemetry circuit 88 and power source 98.

Power source 98 provides power to the circuitry of IMD 14 including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 3, but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for delivering pacing pulses. Power source 98 is also coupled to components of sensing circuit 86, such as sense amplifiers, analog-to-digital converters, switching circuitry, etc., telemetry circuit 88 and memory 82 to provide power to the various circuits as needed.

The functional blocks shown in FIG. 3 represent functionality included in a His bundle pacing device and may include any discrete and/or integrated electronic circuit components that implement analog and/or digital circuits capable of producing the functions attributed to a His bundle pacing device herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for sensing cardiac electrical signals and controlling delivery of cardiac electrical stimulation therapies in response to sensed intrinsic cardiac events, e.g., P-waves attendant atrial depolarization and R-waves attendant ventricular depolarization, or the absence thereof. The available electrodes 20, 22, 24, 26, 28, 30, 32, 34 and housing 15 are electrically coupled to therapy delivery circuit 84 for delivering electrical stimulation pulses to the patient's heart and/or to sensing circuit 86 for sensing cardiac electrical signals produced by the heart, including both intrinsic signals produced by the heart in the absence of a stimulation pulse and evoked response signals produced by the heart in response to a delivered stimulation pulse.

Sensing circuit 86 may include two or more sensing channels for sensing cardiac electrical signals from two or more sensing electrode vectors. For example, a RA signal may be sensed using electrodes 20 and 22, an RV signal may be sensed using electrodes 28 and 30, and a His signal may be sensed using electrodes 32 and 34. In other examples, as shown in FIG. 3, a His bundle near field signal may be sensed by one sensing channel, shown as near field sensing channel 84, for example using electrodes 32 and 34 of His lead 18. A far field signal may be sensed by a second sensing channel, shown as far field sensing channel 89.

As used herein, a "near field" signal refers to a cardiac electrical signal received from a sensing electrode vector including at least one electrode positioned in or proximate to the His bundle, in the vicinity of the site of His pacing pulse delivery, such that the near field signal may also be referred to as a "His bundle near field signal." The His bundle near field signal may or may not include a His bundle evoked response depending on whether the His bundle was captured or not. The His bundle near field signal may include an evoked response QRS waveform signal caused by effective His bundle capture as well as ineffective His bundle capture that may conduct along only a portion of the bundle branch system. The His bundle near field signal may also include an evoked response QRS waveform signal caused by VM capture and loss of His bundle capture.

As used herein, a "far field" signal refers to a cardiac electrical signal received from a pair of electrodes including at least one electrode that is relatively further away from the His bundle than the electrode vector used to sense the His bundle near field signal and/or has a greater inter-electrode distance between the two electrodes defining the far field sensing electrode vector than the inter-electrode distance between the two electrodes defining the His bundle near field sensing electrode vector. The far field signal is more representative of the global activation of the ventricles as opposed to the near field signal being more representative of local tissue activation at or near the pacing site. The far field signal may include an evoked response QRS waveform signal associated with effective His bundle capture, which may be SHB capture or NSHB capture, or ineffective His bundle capture, e.g., during partial His bundle capture resulting in conduction along only part of the bundle branch system, during VM capture with loss of His bundle capture or during complete loss of capture by the His bundle pacing pulse. In the latter case, a QRS waveform signal sensed by the far field sensing channel 89 or the near field sensing channel 87 may be an intrinsic R-wave or an evoked response from a ventricular pacing pulse delivered by RV pacing electrodes 28 and 30.

When the His bundle is captured effectively, the far field QRS width is expected to be narrower than when the His bundle is not effectively captured (and the ventricular myocardial tissue or only part of the conduction system, for example, only the right bundle branch is captured instead). Effective capture of the His bundle resulting in conduction via the intrinsic ventricular conduction system including both the right and left bundle branches generally promotes increased synchrony of the right and left ventricular electrical activation times. This increased synchrony is correlated to a narrower far field QRS width. A relatively wider QRS width is correlated to increased dyssynchrony or heterogeneity of the electrical activation times of the right and left ventricles. A wider QRS width may occur when the His bundle is not captured at all or only partially captured resulting in conduction along only part of the bundle branch conduction system or a depolarization is conducted along a different pathway than the normal, intrinsic ventricular conduction system.

In some examples, the far field signal may be sensed using an electrode carried by RA lead 16 and the IMD housing 15, e.g., electrode 20 and housing 15 or electrode 22 and housing 15. In examples that include RV lead 17, the far field signal may be sensed using RV coil electrode 24 paired with housing 15, SVC coil electrode 26 paired with housing 15, or RV coil electrode 24 paired with SVC coil electrode 26. The His bundle capture detection methods disclosed herein include detecting His bundle capture and may include discriminating between effective His bundle capture and ineffective His bundle capture or loss of His bundle capture using capture detection threshold values established based on a metric of ventricular dyssynchrony as described below.

Sensing circuit 86 may include switching circuitry for selectively coupling a near field sensing electrode pair from the available electrodes to the near field sensing channel 87 for sensing a near field His bundle signal and for selectively coupling a far field sensing electrode pair to far field sensing channel 89 for sensing an electrical signal that is far field relative to the site of delivering His bundle pacing pulses. The far field sensing electrode pair may exclude at least one or both of the electrodes used to deliver the His bundle pacing pulses. Switching circuitry may include a switch array, switch matrix, multiplexer, or any other type of switching device suitable to selectively couple components of sensing circuit 86 to selected electrodes.

Each of near field sensing channel 87 and far field sensing channel 89 may include an input filter for receiving a cardiac electrical signal from a respective sensing electrode pair, a pre-amplifier, an analog-to-digital converter and a bandpass filter for producing a multi-bit digital EGM signal for use in detecting His bundle capture and discriminating between at least effective His bundle capture and ineffective His bundle capture (including complete loss of capture of the His bundle) and may distinguish between SHB, NSHB, and VM capture and/or other types of effective and ineffective capture, such as right bundle branch capture, left bundle branch capture and fusion. Features of the near field and far field EGM signals may be determined by control circuit 80, and in some examples each sensing channel 87 and 89 may include a rectifier to produce a rectified signal from which signal features may be determined by control circuit 80 for use in determining His bundle capture. As described below, the QRS waveform following a His bundle pacing pulse may be used to detect effective His bundle capture and ineffective His bundle capture. The QRS waveform following a His bundle pacing pulse that captures the His bundle and/or the ventricular myocardium may also be referred to herein as an "evoked response signal" and includes the evoked response R-wave that may be sensed by sensing circuit 86.

Sensing circuit 86 may include cardiac event detection circuitry, which may include one or more sense amplifiers, filters, rectifiers, threshold detectors, comparators, analog-to-digital converters (ADCs), timers or other analog or digital components, for detecting cardiac electrical events. For example, an atrial event detector may be included in sensing circuit 86 for detecting intrinsic P-waves attendant to intrinsic atrial depolarizations using one or both of electrodes 20 and 22 carried by RA lead 16. A ventricular event detector may be included in sensing circuit 86 for detecting intrinsic R-waves attendant to intrinsic ventricular depolarizations using electrodes 32 and 34 carried by His lead 18 and/or using electrodes 24, 26, 28 and/or 30 carried by RV lead 17. A cardiac event sensing threshold, such as a P-wave sensing threshold or an R-wave sensing threshold, may be automatically adjusted by sensing circuit 86 under the control of control circuit 80, e.g., based on timing intervals and sensing threshold values determined by control circuit 80, stored in memory 82, and/or controlled by hardware, firmware and/or software of control circuit 80 and/or sensing circuit 86.

Upon detecting a cardiac electrical event based on a sensing threshold crossing, sensing circuit 86 may produce a sensed event signal that is passed to control circuit 80. For example, an atrial event detector may produce a P-wave sensed event signal in response to a P-wave sensing threshold crossing. A ventricular event detector may produce an R-wave sensed event signal in response to an R-wave sensing threshold crossing. The sensed event signals are used by control circuit 80 for setting pacing escape interval timers that control the basic time intervals used for scheduling cardiac pacing pulses. Control circuit 80 may include various timers or counters for counting down an AV pacing interval, a VV pacing interval, an AA pacing interval, etc. A sensed event signal may trigger or inhibit a pacing pulse depending on the particular programmed pacing mode. For example, a P-wave sensed event signal received from sensing circuit 86 may cause control circuit 80 to inhibit a scheduled atrial pacing pulse and schedule a His bundle pacing pulse at the programmed AV pacing interval. If the AV pacing interval expires before control circuit 80 receives an R-wave sensed event signal from sensing circuit 86, control circuit 80 may control therapy delivery circuit 84 to deliver a His pacing pulse at the AV pacing interval following the sensed P-wave and in this way deliver atrial-synchronized ventricular pacing that promotes increased ventricular synchrony. If an R-wave sensed event signal is received from sensing circuit 86 before the AV pacing interval expires, the scheduled His pacing pulse may be inhibited. The AV pacing interval controls the amount of time between an atrial event, paced or sensed, and a His bundle pacing pulse to promote AV synchrony and cause ventricular capture via the His-Purkinje conduction system of the ventricles.

Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse to a selected pacing electrode vector coupled to the therapy delivery circuit 84. Therapy delivery circuit 84 may include one or more pacing channels. In the example of IMD 14, therapy delivery circuit 84 may include an RA pacing channel, a His bundle pacing channel and an RV pacing channel each including a holding capacitor, one or more switches, and an output capacitor for producing pacing pulses delivered by the respective RA lead 16, RV lead 17 and His lead 18. It is recognized that in the case of IMD 14 being a single chamber device configured to receive His lead 18, therapy delivery circuit 84 may include a single pacing channel. In the case of IMD 14 being a dual chamber device configured to receive RA lead 16 and His lead 18, therapy delivery circuit 84 may have an atrial pacing channel and a His pacing channel.

Therapy delivery circuit 84 charges a holding capacitor to a programmed pacing voltage amplitude and discharges of the capacitor for a programmed pacing pulse width according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes or anti-tachycardia pacing sequences. The microprocessor of control circuit 80 may also set the amplitude, pulse width, polarity or other characteristics of the cardiac pacing pulses, which may be based on programmed values stored in memory 82.

Control circuit 80 is configured to perform His bundle capture monitoring by determining one or more features of QRS waveforms of a near-field and/or far-field cardiac electrical signal received from sensing circuit 86. A QRS feature determined following a His bundle pacing pulse is compared to His bundle capture detection threshold established to distinguish effective His bundle capture from ineffective His bundle capture and loss of capture. If the QRS feature meets the capture detection threshold requirement, effective His bundle capture is detected. If not, ineffective capture of His bundle may be detected which may include loss of His bundle capture or only partial capture of His bundle conduction system. Control circuit 80 may control therapy delivery circuit 84 to adjust the pacing pulse output, e.g., increase pacing pulse voltage amplitude and/or pulse width, in response to detecting loss of capture or ineffective His bundle capture in order to maintain effective His bundle capture and promote improved electrical synchrony of the right and left ventricles.

The appropriate capture detection threshold applied to a QRS waveform feature by control circuit 80 for detecting effective His bundle capture may vary between patients, electrode location, sensing electrode vector (e.g., near-field or far-field, etc.), His bundle pacing system and other factors. In some cases, a change in the EGM signal produced by the His bundle pacing device due to effective His bundle capture may be difficult to discern from ineffective His bundle capture, particularly from a relatively near-field signal that may not fully reflect an increase in the global electrical homogeneity or synchronicity of the right and left ventricles following an effective His bundle pacing pulse. The techniques disclosed herein provide an external computing apparatus as described below in conjunction with FIG. 4 for identifying effective His bundle capture with a high degree of certainty from cardiac electrical signals received from body surface electrodes. The His bundle pacing device, e.g., IMD 14, is notified that effective His bundle capture is identified by the computing apparatus and is configured to establish a His bundle capture detection threshold in response to the notification. The His bundle capture detection threshold may be based on a QRS waveform feature determined in response to being notified of the confirmed effective His bundle capture.

Control parameters utilized by control circuit 80 for sensing cardiac events, and controlling pacing therapy delivery may be programmed into memory 82 via telemetry circuit 88. Telemetry circuit 88 includes a transceiver and antenna for communicating with an external device 50 (FIG. 1) using radio frequency communication or other communication protocols. Under the control of control circuit 80, telemetry circuit 88 may receive downlink telemetry from and send uplink telemetry to the external device 50.

In some examples, telemetry circuit 88 is configured for bidirectional radio frequency communication with an external computing apparatus configured to identify His bundle capture as described below. In some examples, telemetry circuit 88 is a BLUETOOTH® enabled circuit configured to receive a His bundle capture notification from external device 50 or other external computing apparatus configured to identify effective His bundle capture from body surface cardiac electrical signals, e.g., electrocardiogram (ECG) signals. As described in conjunction with FIGS. 4-10, IMD 14 or pacemaker 100 may respond to a His bundle capture notification received from an external computing device by establishing a His bundle capture detection threshold for use in His bundle capture monitoring.

Figure 4:
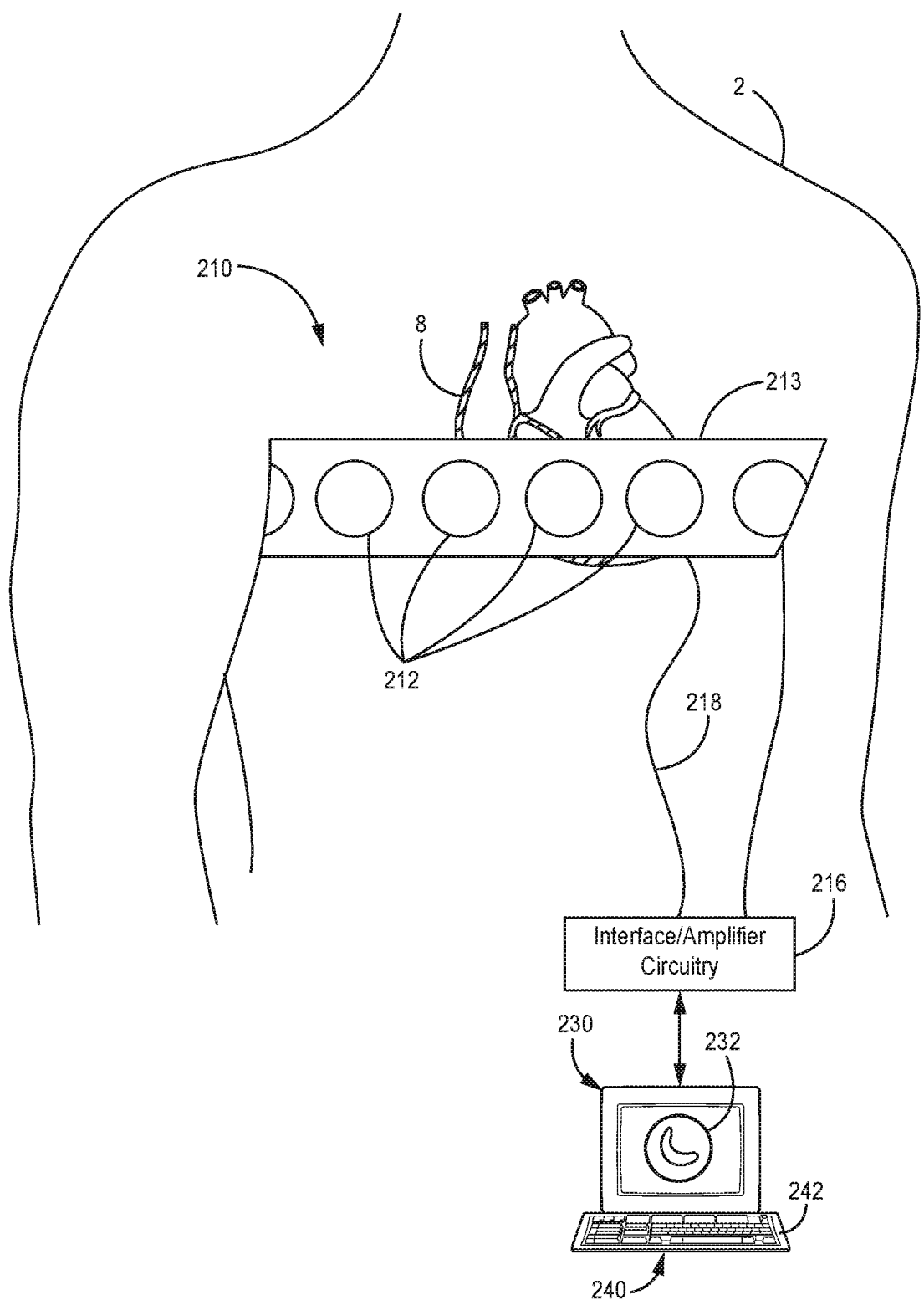
FIG. 4 is a conceptual diagram of a medical device system including a computer apparatus for generating electrical activation information of the patient's heart during His bundle pacing by a His bundle pacing device.

FIG. 4 is a conceptual diagram of a system 200 for evaluating electrical activation information of the patient's heart 8 during His bundle pacing by a His bundle pacing device, such as IMD 14 shown in FIG. 1 or pacemaker 100 shown in FIG. 2. While a His bundle pacing device is not seen in the view of FIG. 4, it is to be understood that system 200 is used in conjunction with a His bundle pacing device configured to deliver His bundle pacing pulses to heart 8. System 200 can be used in conjunction with the His bundle pacing device to establish a His bundle capture detection threshold that is applied to a feature of the cardiac electrical signal received by the His bundle pacing device for monitoring for and detecting effective His bundle capture.

System 200 includes electrode apparatus 210, interface/amplifier circuitry 216, and computing apparatus 240. The electrode apparatus 210 includes a plurality of electrodes 212 that may be carried by a substrate 213 that is attachable or wearable by the patient, e.g., a band strapped around the chest or torso of patient 2. The electrode apparatus 210 is operatively coupled to the computing apparatus 240 via interface/amplifier circuitry 216 (e.g., through wired electrical connections, wirelessly, etc.) to provide electrical signals from each of the electrodes 212 to the computing apparatus 240 for analysis for identifying His bundle capture. The electrode apparatus 210 may generally correspond to the bioelectric sensor device described in U.S. Pat. No. 9,320,446 (Gillberg, et al.) or the surface bio-potential sensing device generally described in U.S. Pat. No. 8,972,228 (Ghosh, et al.), both of which patents are incorporated herein by reference in their entirety.

The dispersion of electrical activation times of the patient's heart may be evaluated to detect effective His bundle capture by pacing pulses being delivered to heart 8 by the His bundle pacing device, e.g., IMD 14 or pacemaker 100. The more heterogeneous or dyssynchronous the electrical activation times of the patient's ventricles, the less likely the His bundle has been captured effectively by a His bundle pacing pulse. Electrical activation times indicative of relatively homogenous or synchronous electrical activation of the ventricles indicate effective His bundle capture. Electrical activation information or data from one or more regions of a patient's heart may be monitored, or determined, using electrode apparatus 210. Electrode apparatus 210 may be configured to measure body-surface potentials of a patient 2 and, more particularly, torso-surface potentials of a patient 2, also referred to herein as body surface cardiac electrical signals. As shown in FIG. 4, electrode apparatus 210 may include a set, or array, of electrodes 212 configured on substrate 213 to be wrapped around the torso of patient 2 such that the electrodes 212 surround the patient's heart 8. The electrodes 212 may be positioned around the circumference of patient 2, including the posterior, lateral, posterolateral, anterolateral, and anterior locations of the torso of patient 2.

Electrodes 212 may be electrically connected to interface/amplifier circuitry 216 via wired connection 218. The interface/amplifier circuitry 216 may be configured to filter and amplify the electrical signals from electrodes 212 and provide the amplified signals to the computing apparatus 240, e.g., as channels of data. For instance, interface/amplifier circuit 216 may include an input filter and amplifier, an analog-to-digital converter, and an output amplifier for producing a surface biopotential or ECG signal from each of electrodes 212. In some examples, system 200 may include wireless communication for transmitting the signals from the interface/amplifier circuitry 216 to the computing apparatus 240. For example, the interface/amplifier circuitry 216 may be electrically coupled to the computing apparatus 240 by analog electrical connections, digital electrical connections, wireless connections, bus-based connections, network-based connections, internet-based connections, etc.

Although in the example of FIG. 4 the electrode apparatus 210 includes an electrode substrate 213 in the form of a strap or band that can be wrapped around the torso of patient 2, in other examples any of a variety of substrates, e.g., tape, adhesives, vest, jacket or other substrate, may be employed to aid in the spacing, placement and contact of electrodes 212 along the patient's torso, surrounding heart 8. In some examples, the substrate 213 may include an elastic band, strip of tape, or cloth. In other examples, the electrodes 212 may be placed individually on the torso of a patient 2, e.g. using adhesive pads as the electrode substrate. Further, in other examples, electrodes 212 (e.g., arranged in an array) may be part of, or located within, patches, vests, and/or other manners of securing the electrodes 212 to the torso of patient 2.

Figure 5:
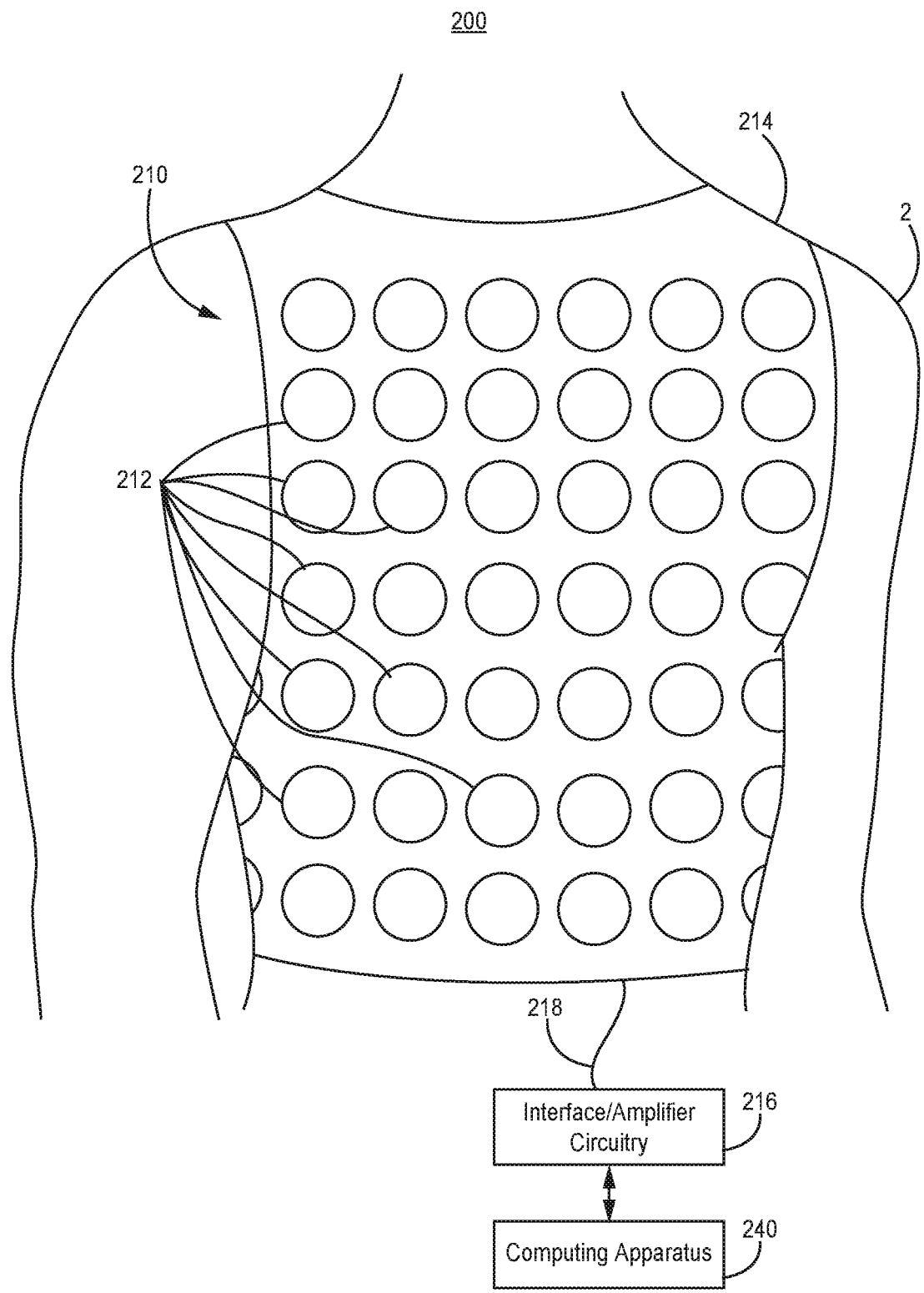
FIG. 5 is a conceptual diagram of the electrode apparatus of FIG. 4 according to another example.

FIG. 5 is a conceptual diagram of electrode apparatus 210 according to another example. In this example, multiple spaced apart electrodes 212 are carried by a substrate 214 configured as a vest configured to distribute the electrodes 212 along the torso of the patient 2 and hold the electrodes 212 in close proximity or direct contact with the skin of the patient for sensing surface biopotential signals arising from the electrical activity of the patient's heart. As illustrated, the electrodes 212 may be distributed over the torso of patient 2 and may circumscribe the torso, including, for example, the anterior, lateral, posterolateral, anterolateral, and posterior surfaces of the torso of patient 2.

The substrate 214 may be formed of fabric with the electrodes 212 attached to the fabric. The substrate 214 may be configured to maintain the position and spacing of electrodes 212 on the torso of patient 2 and may be marked to assist in determining the location of the electrodes 212 on the surface of the torso of patient 2. In one example, substrate 214 includes 17 or more anterior electrodes positionable proximate the anterior torso of the patient, and 39 or more posterior electrodes positionable proximate the posterior torso of the patient. In some examples, there may be about 25 electrodes to about 256 electrodes carried by substrate 214 for distribution around the torso of patient 2, though other configurations may have more or less electrodes 212.

As described herein, the electrode apparatus 210 may be configured to measure electrical information (e.g., electrical signals) representing different regions of a patient's heart. For example, activation times of different regions of a patient's heart can be approximated from activation times determined from surface potential signals received from electrodes 212 in proximity to regional body surface areas corresponding to the different regions of the patient's heart.

Referring generally to system 200 shown in FIGS. 4 and 5, electrodes 212 are carried by a selected substrate configured to surround heart 8 for recording or monitoring the cardiac electrical signals attendant to the depolarization and repolarization of the heart after the signals have propagated through the torso of patient 2. Each of the electrodes 212 may be used in a unipolar configuration to sense the torso-surface potentials that reflect the cardiac signals. The interface/amplifier circuitry 216 may also be coupled to a return or indifferent electrode (not shown) that may be used in combination with each electrode 212 for unipolar sensing. In some examples, there may be about 12 to about 50 electrodes 212 spatially distributed around the torso of patient 2. Other configurations may have more or fewer electrodes 212. The size, number and arrangement of electrodes 212 on substrate 213 or 214 and relative to heart 8 shown in FIG. 4 and FIG. 5, respectively, are intended to illustrate the concept of an electrode apparatus that may be employed in the system 200 with no limitations intended.

The computing apparatus 240 may record and analyze the electrical signals (e.g., torso-surface potential signals) sensed by electrodes 212 and filtered and amplified by the interface/amplifier circuitry 216. The computing apparatus 240 may be configured to analyze the signals from the electrodes 212 to provide anterior and posterior electrode signals and cardiac electrical activation times, e.g., representative of actual, or local, electrical activation times of one or more regions of the patient's heart. For example, the electrical signals received by electrodes positioned at the left anterior surface location of a patient's torso may be representative of electrical signals of the left anterior left ventricle region of the patient's heart. Electrical signals received by electrodes positioned at the left lateral surface location of a patient's torso may be representative of electrical signals of the left lateral left ventricle region of the patient's heart. Electrical signals received by electrodes positioned at the left posterolateral surface location of a patient's torso may be representative of electrical signals of the posterolateral left ventricle region of the patient's heart. Electrical signals received by electrodes positioned at the posterior surface location of a patient's torso may be representative of electrical signals of the posterior left ventricle region of the patient's heart and so on.

His bundle pacing can provide a more synchronized, homogeneous electrical activation of the right and left ventricles of the heart compared to pacing from other sites in or on the ventricles because a depolarization caused by a His bundle pacing pulse that effectively captures the His bundle can be conducted through the natural, intrinsic conduction system of the ventricles. Characterization of the spatial electrical activation of the ventricles using system 200 may be performed during His bundle pacing by a His bundle pacing device to determine when His bundle pacing pulses are capturing the His bundle effectively with a high degree of certainty based on reduction in ventricular dyssynchrony, also sometimes referred to as "electrical heterogeneity." This determination is used to notify the His bundle pacing device when effective His bundle capture is confirmed to enable the His bundle pacing device to establish a His bundle capture detection threshold used by the His bundle pacing device for His bundle capture monitoring and discrimination between effective and ineffective His bundle capture.

Body-surface isochronal maps of ventricular activation can be constructed using the monitored electrical activity during His bundle pacing at different pacing pulse output settings and/or in the absence of His bundle pacing. The monitored electrical activity and/or the map of ventricular activation can be used to generate electrical dyssynchrony data. The electrical dyssynchrony data can include determining metrics of electrical dyssynchrony. A metric of electrical dyssynchrony, which may also be referred to as a metric "electrical heterogeneity," is an indication of the temporal dispersion of electrical activation times over the ventricles. A metric of electrical dyssynchrony may be determined from the QRS waveforms of the electrical signals received from electrodes 212, spatially dispersed over the torso of the patient and surrounding heart 8. For example, the time of electrical activation of a region of the ventricle may be determined as the time interval from an onset of the QRS waveform to a fiducial point of the QRS waveform. In some examples, the electrical activation time is the time from the onset of a QRS waveform to a maximum slope of the QRS waveform. For instance, the electrical activation time is determined as the time from the onset of the QRS waveform to a maximum negative slope of the QRS waveform. An example method for determining the electrical activation time is described below in conjunction with FIG. 7.

Computing apparatus 240 may be configured to determine metrics of electrical dyssynchrony by determining an electrical activation time from each of the cardiac electrical signals received from electrodes 212, or a selected subset thereof, and determine a standard deviation of those electrical activation times (SDAT). In some examples, the mean and/or standard deviation may be determined from the electrical signals received from electrodes on the left side of the torso of the patient to obtain a metric of electrical dyssynchrony of the left ventricle. For example, a mean of the left ventricular activation times (LVAT) may be determined. The metric of LVAT may be determined from electrodes on both the anterior and posterior surfaces along the left side of the patient 2. The metrics of electrical dyssynchrony may include a metric of mean right ventricular activation time (RVAT) of electrodes on the right side of the torso of the patient. A metric of RVAT may be determined from electrodes on both the anterior and posterior surfaces along the right side of patient 2. The metrics of electrical dyssynchrony may include a mean total activation time (MTAT) taken from a plurality of electrode signals from both right and left sides of the torso of the patient (from anterior and/or posterior surface of the patient 2), and/or it may include other metrics (e.g., standard deviation, interquartile deviations, a difference between a latest activation time and earliest activation time as examples) correlated to or corresponding to a range or dispersion of activation times as sensed by multiple, spaced apart electrodes located on the right side of the patient torso, the left side of the patient torso, or a combination of both right and left sides of the patient torso, including posterior, anterior and/or laterally positioned electrodes.

Assessment of electrical dyssynchrony of the ventricles during His bundle pacing for establishing a capture detection threshold by the His bundle pacing device may include determination of at least one of SDAT, LVAT, RVAT, and MTAT. As an example, effective His bundle capture may be detected by computing apparatus 240 in response to an SDAT generated during His bundle pacing that is less than a selected SDAT threshold value. As an example, a selected SDAT threshold may be less than or equal to 25 milliseconds (ms) or another selected threshold, which may be patient specific, to discriminate effective His bundle capture from ineffective His bundle capture. His bundle pacing may be withheld in patient's having intact AV conduction so that a baseline electrical dyssynchrony metric may be determined when His bundle pacing is withheld. In this case, His bundle capture may be identified when SDAT is reduced compared to no His bundle pacing, e.g., a relative change in SDAT. If the patient has AV conduction block and is therefore dependent on ventricular pacing, a metric of electrical dyssynchrony may be determined during RV pacing (when RV pacing electrodes are available such as with IMD 14 of FIG. 1). For instance, effective His bundle capture may be identified when SDAT decreases during His bundle pacing compared to SDAT determined during RV pacing.

In other examples, effective His bundle capture may be detected based on an LVAT being below a selected threshold during His bundle pacing. The selected threshold corresponding to an LVAT indicative of effective His bundle capture may be less than or equal to 35 ms as an example. In at least one example, effective His bundle capture is identified in response to both the SDAT and the LVAT generated during His bundle pacing being below selected thresholds for each. In still other examples, effective His bundle capture may be detected in response to an RVAT and/or MTAT generated during His bundle pacing therapy being below a selected threshold. In other examples, the His bundle pacing device is configured to deliver His bundle pacing pulses at multiple pacing pulse outputs, e.g., at multiple pacing pulse amplitudes, and computing apparatus 240 identifies His bundle capture when the SDAT, LVAT, RVAT, and/or MTAT is at a minimum or relatively reduced value compared to the same metric value obtained during His bundle pacing at a different pacing pulse output.

Additionally, the computing apparatus 240 may be configured to produce a display or graphical user interface depicting the electrical activation times and/or electrical dyssynchrony data obtained using the electrode apparatus 210. In various examples, the computing apparatus 240 may be a server, a personal computer, or a tablet computer and may include a user input apparatus 242 and a display apparatus 230. The computing apparatus 240 may be configured to receive input from input apparatus 242 and transmit output to the display apparatus 230 (FIG. 4). Further, the computing apparatus 240 may include data storage that may allow for access to processing programs or routines and/or one or more other types of data, e.g., for driving a graphical user interface (GUI) configured to non-invasively identify His bundle capture.

The computing apparatus 240 may be operatively coupled to the input apparatus 242 and the display apparatus 230 to, e.g., to transmit data to and from each of the input apparatus 242 and the display apparatus 230. For example, the computing apparatus 240 may be electrically coupled to each of the input apparatus 242 and the display apparatus 230 using, e.g., analog electrical connections, digital electrical connections, wireless connections, bus-based connections, network-based connections, internet-based connections, etc. As described further herein, a user may provide input to the input apparatus 242 to manipulate, or modify, one or more graphical depictions displayed on the display apparatus 230 and to view and/or select one or more pieces of information related to the electrical activation data.

Although as depicted the input apparatus 242 is a keyboard, it is to be understood that the input apparatus 242 may include any apparatus capable of providing input to the computing apparatus 240 to perform the functionality, methods, and/or logic described herein. For example, the input apparatus 242 may include a mouse, a trackball, a touchscreen (e.g., capacitive touchscreen, a resistive touchscreen, a multi-touch touchscreen, etc.), etc. Likewise, the display apparatus 230 may include any apparatus capable of displaying information to a user, such as a graphical user interface 232 including cardiac electrical signal information, textual instructions, graphical or tabular depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 230 may include a liquid crystal display, an organic light-emitting diode screen, a touchscreen, a cathode ray tube display, etc.

Data stored and/or used by the computing apparatus 240 may include, for example, electrical signal/waveform data from the electrode apparatus 210, parts or portions of various signals received from electrode apparatus 210, electrical activation times determined from signals received from electrode apparatus 210, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical dyssynchrony metrics and His bundle capture or non-capture determination), or any other data that may be necessary for carrying out the one and/or more processes or methods described herein.

Computing apparatus 240 may be configured to generate a notification of His bundle capture identification in response to electrical activation data meeting effective His bundle capture detection criteria. The notification may be generated on display 230 of computing apparatus 240. The notification may include an audible notification in the form of a beep, tone, voiced or other sound. In some examples, the notification includes a wirelessly transmitted signal indicating His bundle capture detection. The His bundle pacing device may be configured to receive a transmitted notification directly from computing apparatus 240, e.g., via a BLUETOOTH® or other wireless connection. The His bundle pacing device may respond by establishing a His bundle capture detection threshold as described below in conjunction with FIG. 8.

The computing apparatus 240 may be, for example, any fixed or mobile computer system (e.g., a controller, a microcontroller, a personal computer, minicomputer, tablet computer, etc.) and may be generally described as including processing circuitry. The exact configuration of the computing apparatus 240 is not limiting, and essentially any device capable of providing suitable computing capabilities and control capabilities (e.g., graphics processing, etc.) may be used. Providing software, hardware, and/or firmware to accomplish the described functionality in the context of any modern medical device system, given the disclosure herein, is within the abilities of one of skill in the art. As such, the computer language, the computer system, or any other software/hardware which is to be used to implement the processes described herein shall not be limiting on the scope of the systems, processes or programs (e.g., the functionality provided by such systems, processes or programs) described herein. In some examples, the functions attributed to computing apparatus 240 may be incorporated in external device 50 of FIG. 1 such that a programmer used to communicate with the His bundle pacing device for programming pacing and sensing control parameters and retrieving data from His bundle pacing device may be configured to generate electrical dyssynchrony data from signals received from electrode apparatus 210, detect effective His bundle capture from the electrical dyssynchrony data, and transmit a notification of His bundle capture to the His bundle pacing device.

Figure 6:
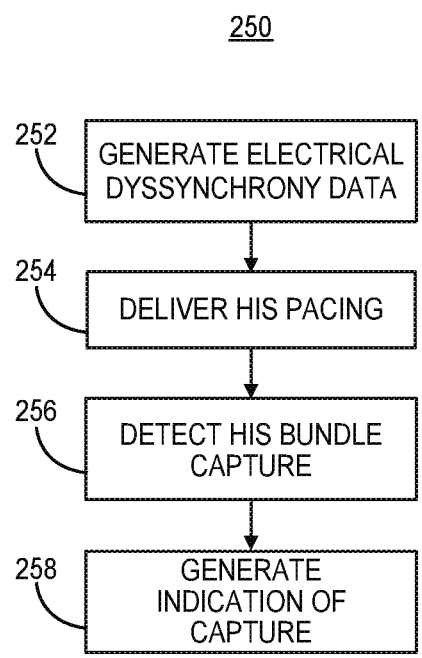
FIG. 6 is a flow chart of a method for identifying His bundle capture by the computing apparatus of FIG. 4 during His bundle pacing according to one example.

FIG. 6 is a flow chart 250 of a method for identifying His bundle capture by computing apparatus 240 during His bundle pacing according to one example. The method of flow chart 250 is performed by system 200 during His bundle pacing delivered by a His bundle pacing device, such as IMD 14 or pacemaker 100. At block 252, electrical dyssynchrony data are generated by computing apparatus 240. Electrical dyssynchrony data may include SDAT, LVAT, RVAT, MTAT or other metric(s) of the temporal dispersion of electrical activation of the ventricles derived from the cardiac electrical signals received from electrode apparatus 210. Computing apparatus 240 may generate electrical dyssynchrony data prior to or while withholding His bundle pacing by the His bundle pacing device. By generating electrical dyssynchrony data prior to or while withholding His bundle pacing, computing apparatus 240 may generate baseline or His bundle non-capture electrical dyssynchrony data for comparative analysis to electrical dyssynchrony data generated during delivery of His bundle pacing. In a pacing dependent patient, RV pacing may be delivered, e.g., using RV lead 17, when His bundle pacing is being withheld to avoid ventricular asystole while generating electrical dyssynchrony data corresponding to His bundle non-capture.

Figure 7:
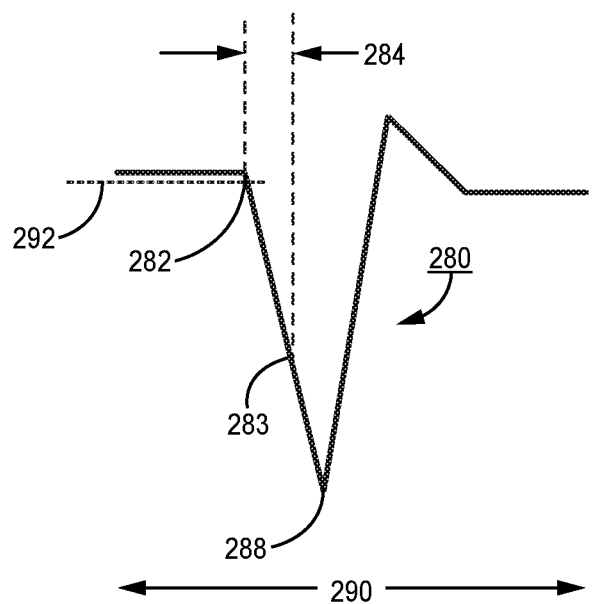
FIG. 7 depicts one method for determining an electrical activation time from at least one QRS waveform of a given surface potential signal received from an electrode of the electrode apparatus of FIG. 4 or FIG. 5.

Computing apparatus 240 may generate electrical dyssynchrony data at block 252 by determining an electrical activation time from one or more QRS waveforms of each cardiac electrical signal (or selected subset of cardiac electrical signals) received from electrode apparatus 210. FIG. 7 is a conceptual diagram of a QRS waveform and a method that may be performed by computing apparatus 240 for determining electrical activation time. The illustrated QRS waveform 280 is depicted as a net negative going waveform in this example. In various examples, the QRS waveform may be a net negative or net positive complex and may have areas that exceed a baseline signal (positive areas) and areas that are less than the baseline signal (negative areas). The electrical activation time 284 may be determined as the time point at which a maximum negative slope 283 of the QRS waveform 280 occurs. The electrical activation time 284 may be determined relative to a QRS onset 282. In this example, the electrical activation time 284 may be determined as the time from QRS onset 282 (considered time 0 ms) until the steepest negative slope 283 of QRS waveform 280. Accordingly, computing apparatus 240 may include a differentiator or algorithm for computing consecutive differences between QRS waveform sample points to identify the maximum negative slope of the QRS waveform 280, in this example on the leading portion of the QRS waveform 280, earlier than the maximum peak 288.

The QRS onset 282 may be determined by identifying a minimum sample point of the QRS waveform 280 prior to peak 288 but within a QRS time window 290. In other examples, QRS onset 282 may be determined by identifying the latest sample point of QRS waveform 280 that occurs prior to peak 288 and with an absolute value equal to or less than a predetermined threshold 292. For example, threshold 292 may be set to 110% (or other selected percentage) of a minimum absolute value sample point of the QRS waveform 280 detected prior to peak 288 but within window 290. Window 290 may be defined as a predetermined time interval extending from a delivered pacing pulse or sensed cardiac event, e.g., a sensed P-wave or previously sensed R-wave. Alternatively, window 290 may be defined relative to peak 288 or relative to a QRS sensing threshold crossing.

In other examples, the QRS onset 282 may be identified by generating a dispersion waveform from multiple QRS waveforms and detecting an onset of the dispersion waveform as generally disclosed in pre-grant U.S. Patent Application Publication 2018/0263522 (Ghosh, et al.), incorporated herein by reference in its entirety. For example, a dispersion signal may be generated from multiple QRS waveforms as a signal that represents the electrical dispersion of the QRS waveforms over time. In one example, the dispersion signal is generated by determining standard deviations of the sample points of multiple QRS waveforms. An onset of the dispersion signal may be determined as the onset of the QRS waveform.

The time of the maximum slope 283 relative to an identified QRS onset 282 may be stored as the electrical activation time of a cardiac location corresponding to the electrode position of electrode apparatus 210 from which the QRS waveform 280 was received. While a single QRS waveform is shown in FIG. 7, the electrical activation time for a given electrode "channel" during His bundle pacing may be determined from multiple QRS waveforms received from a given electrode or from a time averaged, filtered or dispersion waveform generated from multiple QRS waveforms as a representative QRS waveform of the cardiac electrical signal corresponding to a location or region of the patient's heart.

FIG. 7 depicts one method for determining an electrical activation time from at least one QRS waveform of a given electrode signal. An electrical activation time may be determined using alternate starting, onset or reference time points and subsequent electrical activation time points defined as fiducial points of the QRS waveform during a QRS window and indicative of the electrical depolarization time of a corresponding region of the heart. For example, an electrical activation time may be determined as the time from onset 282 to R-wave peak 288, to a predetermined percentage of R-wave peak 288, etc.

Returning to FIG. 6, at block 254, a His bundle pacing device delivers His bundle pacing according to programmed pacing output control parameters. Computing apparatus 240 generates electrical dyssynchrony data during delivery of His bundle pacing at block 254. At block 256, the computing apparatus 240 identifies when effective His bundle capture occurs based on the electrical dyssynchrony data. In some examples, computing apparatus 240 may compare one or more electrical dyssynchrony metrics to a threshold value that is indicative of acceptable electrical activation synchrony or homogeneity. For example, effective His bundle capture may be detected if SDAT is less than 25 ms. Additionally or alternatively, criteria for detecting effective His bundle capture may include an RVAT less than 30 ms, an LVAT less than 30 ms and/or MTAT less than 50 ms, as examples.

In some examples, computing apparatus 240 may identify or detect effective His bundle capture in response to detecting a relative change in an electrical dyssynchrony metric, e.g., one or more of SDAT, LVAT, RVAT and MTAT, determined during His bundle pacing compared to the analogous metric determined as a baseline metric, e.g., when His bundle pacing is not being delivered (during intrinsic patient rhythm or during RV pacing). A threshold decrease in an electrical dyssynchrony metric that results in effective His bundle capture detection may be 10%, 20%, 25%, 30%, or other predetermined percentage or threshold change. In still other examples, His bundle pacing may be delivered by the His bundle pacing device at multiple pacing pulse outputs, e.g., at multiple pacing pulse voltage amplitudes as electrical dyssynchrony data is being generated by computing apparatus 240. Effective His bundle capture may be detected by computing apparatus 240 at block 256 based on one or more electrical dyssynchrony metrics reaching a threshold or maximum decrease from a maximum value of the metric determined as the His bundle pacing output is varied. As such, effective His bundle capture may be detected based on a relative decrease in SDAT, LVAT, RVAT and/or MTAT as His bundle pacing pulse energy is increased or decreased (or randomly varied).

In some examples, computing apparatus 240 may be configured to identify different types of capture associated with His bundle pacing at block 256. For instance, in some patients, incomplete capture of the His bundle may occur resulting in capture of the right bundle branch (RBB) or the left bundle branch (LBB) but not both. Computing apparatus 240 may generate electrical dyssynchrony data by determining a right ventricular metric of electrical activation times, e.g., RVAT, from QRS waveforms received from the electrode apparatus 210 corresponding to cardiac electrical signals received along a right side of the patient and determining a left ventricular metric of electrical activation times, e.g., LVAT, from QRS waveforms received from the electrode apparatus 210 corresponding to cardiac electrical signals received along a left side of the patient. Computing apparatus 240 may compare the right ventricular metric and the left ventricular metric to a respective right bundle branch capture threshold and left bundle branch capture threshold to identify ineffective His bundle capture. For example, in response to at least one of the right ventricular metric or the left ventricular metric not meeting the respective right bundle branch capture threshold or left bundle branch capture threshold, ineffective His bundle capture may be identified. To illustrate, if RVAT is less than 30 ms (or other selected threshold) but LVAT is greater than 30 ms (or other selected threshold), capture of the RBB and loss of capture of the LBB is identified, resulting in an identification of ineffective His bundle capture. The His bundle pacing device may respond to an ineffective His bundle capture notification by increasing the pacing pulse output, which may result in effective His bundle capture with conduction along both the LBB and RBB.

In some instances, a His bundle pacing pulse may capture ventricular myocardial tissue (VM capture) without capturing the His bundle when the His bundle capture threshold is greater than the ventricular myocardial capture threshold. Effective capture of the His bundle at a higher pacing pulse output results in effective His bundle capture which may include capture of the surrounding ventricular myocardium, i.e., non-selective His bundle capture. Computing apparatus 240 may be configured to distinguish between effective His bundle capture and ineffective His bundle capture (which may include only partial activation of the conduction system or only VM capture or complete loss of capture) based on electrical dyssynchrony data. In some cases, a relatively lower His bundle pacing pulse that captures the ventricular myocardium without capturing the His bundle may be delivered to establish baseline electrical dyssynchrony data during His bundle non-capture. Computing apparatus 240 may generate electrical dyssynchrony data as the His bundle pacing pulse output is increased until effective His bundle capture is achieved so that computing apparatus 240 may identify effective His bundle capture based on a comparison to the electrical dyssynchrony data generated during VM capture. In other examples, effective His bundle capture may be distinguished from ineffective His bundle capture by computing apparatus 240 as the pacing pulse output is decreased from an initially high level, until partial capture of His bundle or VM only capture is identified, and then decreased further until complete loss of capture is identified.

When computing apparatus 240 determines that the electrical dyssynchrony data meets effective His bundle capture criteria at block 256 based on the comparative analysis of one or more electrical dyssynchrony metrics to predefined thresholds or relative changes in the one or more metrics, computing apparatus may generate an indication of His bundle capture at block 258. An indication of His bundle capture may include a notification produced on display 230 or a GUI of computing apparatus 240, producing an audible signal, transmitting a wireless or wired signal to external device 50 (FIG. 1) for transmission to the His bundle pacing device or transmitting a wireless signal directly to the His bundle pacing device as examples. When the indication of His bundle capture is generated as a notification on a display 230 or GUI of computing apparatus 240, a user may transmit the notification to the His bundle pacing device by a wireless communication signal, e.g., a BLUETOOTH® signal, directly from computing apparatus 240 or by entering a command in another external device 50 (FIG. 1) to transmit the notification to the His bundle pacing device. In other examples, the His bundle capture notification is transmitted by computing apparatus 240 to the His bundle pacing device upon effective His bundle capture detection by computing apparatus 240 without requiring user intervention.

In some examples, the pacing output control parameters may be varied by the His bundle pacing device during His bundle pacing. For instance, a predetermined number of pacing pulses may be delivered at each of a plurality of pacing pulse voltage amplitudes, e.g., 5 to 20 pulses or more may be delivered at each one of two or more pacing pulse voltage amplitudes delivered in 0.25 V, 0.5 V, 1.0 V or other selected voltage increments or decrements. Computing apparatus 240 may detect effective His bundle capture at block 256 based on the electrical dyssynchrony data generated during His bundle pacing at the different pacing pulse voltage amplitudes (and/or pulse widths). Computing apparatus 240 generates an indication of capture at block 258 in response to identifying effective His bundle capture. In some examples, computing apparatus 240 may identify when His bundle loss of capture or ineffective His bundle capture is identified and generate an indication of ineffective His bundle capture at block 258. In this way, the His bundle pacing device may receive a notification or confirmation of both conditions of effective His bundle capture and ineffective His bundle capture.

When computing apparatus 240 is configured to distinguish between different types of His bundle capture, e.g., ineffective His bundle capture resulting in RBB or LBB capture but not both or NSHB vs. SHB capture, computing apparatus 240 may generate different distinct notifications to indicate the type of capture detected. In this way, when an ineffective His bundle capture notification is generated, the His bundle pacing device may respond to the notification by increasing the pacing output in an attempt to fully capture the His bundle and wait for confirmation from the computing apparatus 240 that effective His bundle capture is identified. In some examples, computing apparatus 240 may generate notifications when NSHB capture is identified and when SHB capture is identified as the His bundle pacing output is varied.

By generating an indication of His bundle capture at block 258, computing apparatus 240 provides a notification that can be transmitted to the His bundle pacing device, either directly or indirectly via another device, for use by the His bundle pacing device in establishing a His bundle capture detection threshold. The His bundle pacing device is thereby enabled to establish a His bundle capture detection threshold by determining a cardiac electrical signal feature, in response to receiving the notification generated by computing apparatus 240 while effective His bundle capture is confirmed to be occurring by computing apparatus 240. A feature of the cardiac electrical signal during ineffective His bundle capture (including His bundle loss of capture) may also be determined by the His bundle pacing device to facilitate selection of a His bundle capture detection threshold by the His bundle pacing device that reliably distinguishes effective His bundle capture from ineffective types of capture that may occur during His bundle pacing. A His bundle capture threshold may be established by the control circuit 80 (FIG. 3) of the His bundle pacing device that distinguishes between different types of effective His bundle capture (e.g., SHB and NSHB capture) and between different types of ineffective His bundle capture (e.g., VM only, RBB or LBB capture). In some examples, His bundle pacing device control circuit 80 establishes a QRS feature threshold that distinguishes SHB from NSHB capture. In some instances, SHB capture may be desired and in other instances NSHB capture may be desired, which may depend at least in part on which has the higher capture threshold (and therefore power requirements for generating pacing pulses). Accordingly, computing apparatus 240 may be configured to discriminate between SHB and NSHB capture and generate a notification regarding the type of effective His bundle capture that is detected. His bundle pacing device has the improved capability of tailoring the His bundle capture detection threshold to a given patient and for a specific type of effective His bundle capture (e.g., SHB or NSHB capture) that is desired.

Figure 8:
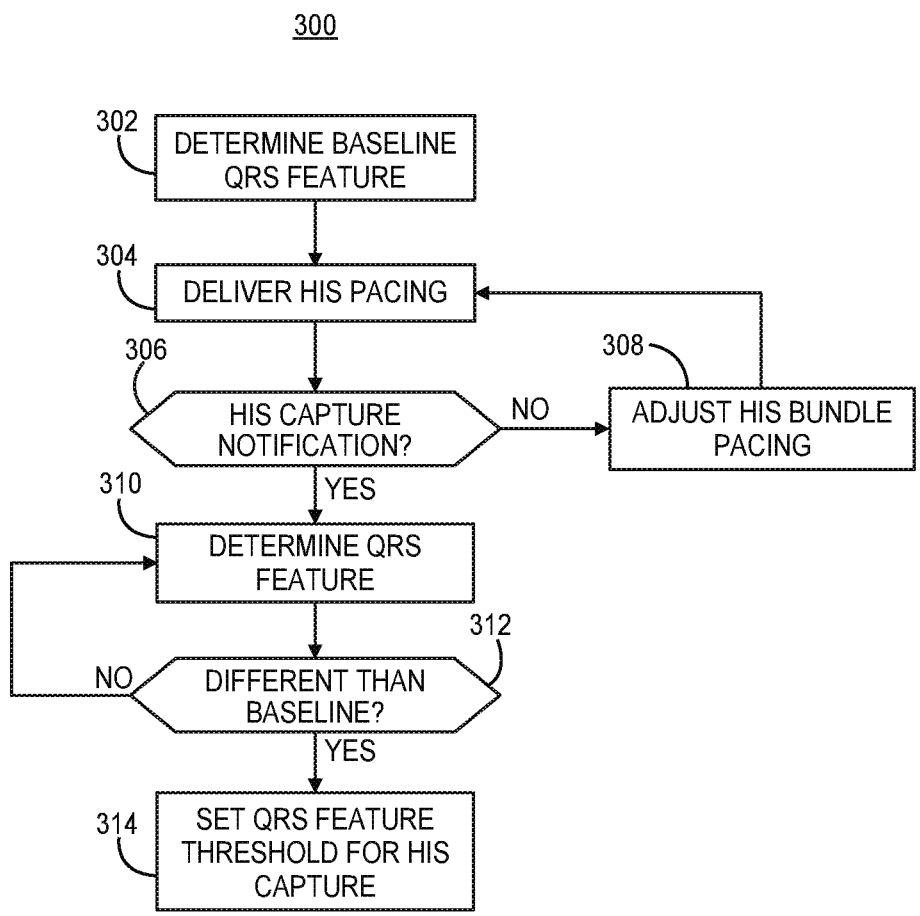
FIG. 8 is flow chart of a method performed cooperatively by the system of FIG. 4 and a His bundle pacing device for establishing a capture detection threshold according to one example.

FIG. 8 is a flow chart 300 of a method performed cooperatively by system 200 and a His bundle pacing device for establishing a capture detection threshold according to one example. At block 302, control circuit 80 of the His bundle pacing device, e.g., IMD 14 or pacemaker 100, may determine a baseline QRS feature from the cardiac electrical signal received from sensing circuit 86. One or more baseline QRS features may be determined from a near field signal received from near field sensing channel 87, from a far field signal received from far field sensing channel 89 or both. The near field and far field signals are produced by the His bundle pacing device sensing circuit, e.g., sensing circuit 86 as described in conjunction with FIG. 3 above. Examples of near field and far field signals that may be produced by cardiac electrical signal sensing circuit of the His bundle pacing device are described below in conjunction with FIG. 9.

A baseline QRS waveform feature determined at block 302 by the His bundle pacing device may include a QRS width and/or QRS area determined from a near field and/or far field signal received from sensing circuit 86. In other examples, the QRS waveform feature determined at block 302 may include a QRS polarity, QRS time delay and/or QRS waveform template representing the overall shape or morphology of the QRS waveform over a specified time window. A combination of two or more features may be determined from a near field signal, from a far field signal or from both near field and far field signals at block 302 for establishing baseline QRS waveform features representative of non-capture of the His bundle. The baseline QRS waveform features may be determined by control circuit 80 when His bundle pacing is being withheld by control circuit 80 or during RV only pacing delivered by therapy delivery circuit 84 in a pacing dependent patient in some examples.

At block 304, the His bundle pacing device delivers His bundle pacing. Control circuit 80 may control therapy delivery circuit 84 to deliver His bundle pacing pulses according to programmed, default or most recently used pacing output control parameters. In some examples, the His bundle pacing pulses are delivered at a predetermined starting pulse output, e.g., pulse voltage amplitude for a given pacing pulse width, that is expected to capture the His bundle. In other examples, the pacing pulse output may be set to a starting low value, e.g., a low pacing pulse voltage amplitude not expected to capture the His bundle, or a starting high value, e.g., a high pacing pulse voltage amplitude expected to capture the His bundle.

At block 306, the His bundle pacing device waits for a His bundle capture notification while generating and delivering the His bundle pacing pulses. The telemetry circuit 88 may receive a wireless communication signal directly from computing apparatus 240 or from another external device 40 indicating that computing apparatus 240 has identified (detected) effective His bundle capture based on the analysis of electrical dyssynchrony metric(s). If a His bundle capture notification is not received within an expected time period (e.g., 30 seconds, one minute, two minutes or other selected time period), or if an ineffective His bundle capture notification is received at block 306, control circuit 80 may adjust the pacing pulse output at block 308. In some examples, the pacing pulse voltage amplitude is increased. In other examples, the pacing pulse width is increased. In still other examples, at least one electrode selected for delivering His bundle pacing pulses may be changed, e.g., by switching circuitry included in therapy delivery circuit 84, when additional His bundle pacing electrode vectors are available.

His bundle pacing is delivered at the adjusted pacing output setting at block 304 by therapy delivery circuit 84, and control circuit 80 waits for a His bundle capture notification at block 306. This process of adjusting a pacing output control parameter at block 308, delivering His bundle pacing using the adjusted control parameter, and waiting for a His bundle capture notification by the His bundle pacing device may be repeated multiple times until effective His bundle capture is confirmed by the computing apparatus 240 and a notification is generated and received by the His bundle pacing device.

Once a His bundle capture notification is received, control circuit 80 determines one or more features of the cardiac electrical signal during the confirmed effective His bundle pacing at the pacing output control parameters associated with the receipt of the His bundle capture notification. For example, the QRS width, QRS area, QRS time delay from the immediately preceding His bundle pacing pulse, QRS polarity, QRS waveform template and/or other QRS features may be determined at block 310. In some examples, control circuit 80 compares the determined feature to the baseline feature at block 312 to verify that a detectable change or difference exists between the QRS feature determined during His bundle capture and the same QRS feature determined during non-capture of the His bundle. If the QRS feature is determined to be substantially unchanged (e.g., within a threshold difference or percentage such as 10% or less), a different QRS waveform feature may be determined at block 310 for use in monitoring for effective His bundle capture.

At block 314, the QRS waveform feature determined during effective His bundle capture is used by control circuit 80 to set a His bundle capture detection threshold. For example, if the QRS width is determined by control circuit 80 at block 310, control circuit 80 of the His bundle pacing device may set the capture detection threshold to the determined QRS width associated with His bundle capture detection plus a small offset, e.g., 5%, 10% or 20% of the QRS width or a fixed offset of 5 ms or other predetermined value, to allow for some variation in the QRS width that may occur during effective His bundle capture. When a baseline QRS feature value is determined during His bundle non-capture, the capture detection threshold established at block 314 may be set to a value that is between the value determined at block 310 and the baseline value determined at block 302, e.g., at a midpoint between the values or at a different portion of the difference.

When computing apparatus 240 is configured to generate a notification corresponding to different types of effective His bundle capture, e.g., SHB and NSHB capture, the His bundle pacing device may determine QRS feature(s) corresponding to a notification of each His bundle capture type and establish a threshold for detecting and discriminating the His bundle capture type at block 314. Criteria for detecting different types of effective (e.g., SHB and NSHB capture) and ineffective His bundle capture (e.g., RBB capture, LBB capture, VM only capture) may be established by control circuit 80 at block 314, with each unique set of criteria involving one or more capture detection thresholds established for a respective one or more QRS features determined from the near field and/or far field cardiac electrical signal sensed the His bundle pacing device.

Figure 9:
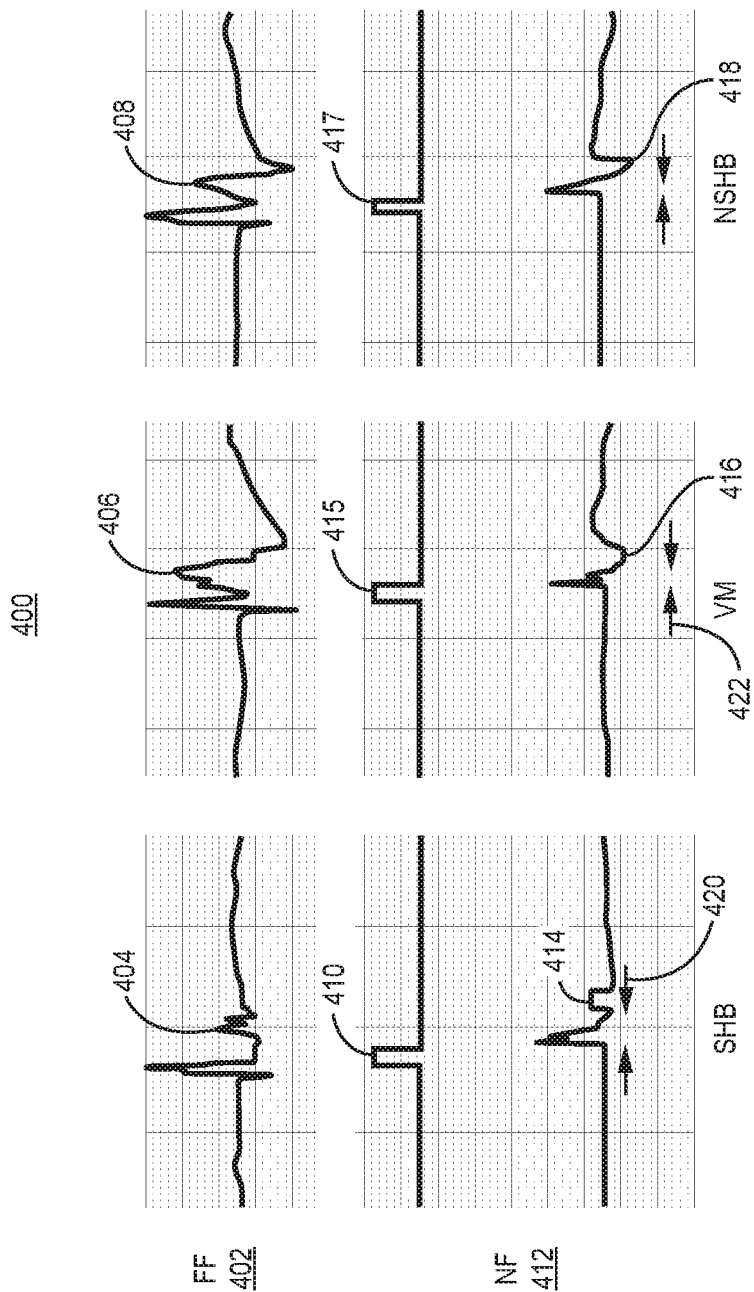
FIG. 9 is a diagram of cardiac electrical signals that may be produced by the His bundle pacing device.

FIG. 9 is a diagram 400 of cardiac electrical signals that may be produced by the His bundle pacing device. The cardiac electrical signals include evoked response QRS waveform signals representing SHB capture (left column), NSHB capture (right column), and VM capture (center column). Far field cardiac electrical signals 402 and corresponding His bundle near field signals 412 are shown aligned in time with a respective His bundle pacing pulse 410, 415 or 417 in each example.

In the left column, the His bundle pacing pulse 410 that results in SHB capture produces a His bundle near field evoked response QRS waveform 414 that occurs after a time delay 420. The His bundle near field QRS waveform 414 during effective His bundle capture has a positive polarity in some patients and relatively narrow signal width. The far field evoked response QRS waveform 404 is also seen to be relatively narrow, positive in polarity and occurring after a time delay. The time delay 420 following the effective His bundle pacing pulse 410 until the QRS waveform 414 is due to the time required for the depolarization to be conducted along the His Purkinje conduction system.

In the middle column, the far field evoked response QRS waveform 406 and the corresponding His bundle near field evoked response QRS waveform 416 following an ineffective His bundle pacing pulse 415 that only captures ventricular myocardial tissue without capturing the His bundle are shown. The near field QRS waveform 416 occurs after a relatively shorter time delay 422 than the time delay 420 of QRS waveform 414 during effective, SHB capture due to the absence of conduction along the His Purkinje conduction system following the ineffective His bundle pacing pulse 415. The near field evoked response QRS waveform 416 during VM capture is relatively wide and has a negative polarity. The wide QRS waveform width is evidence of increased electrical dyssynchrony during ineffective His bundle capture.

The far field QRS waveform 408 and His bundle near field QRS waveform 418 during NSHB capture are shown in the right column. In the His bundle near field signal 412, the QRS waveform 416 (middle column) during ineffective His bundle capture (VM capture) and the QRS waveform 418 (right column) during effective His bundle capture are substantially similar. Both signals 416 and 418 occur early after the respective His bundle pacing pulse 415 and 417, both are negative in polarity and have relatively wider QRS waveform widths than the SHB QRS waveform 414. Accordingly, effective His bundle pacing resulting in SHB capture may be positively detected from the His bundle near field signal 412, e.g., based on the longer time delay 420 until the QRS waveform 414, the positive polarity (at least in some patients), relatively narrow QRS width, relatively small QRS waveform area or any combination thereof. The similarities of the timing and morphology of the His bundle near field evoked response signal 418 during effective, NSHB capture and the near field evoked response signal 416 during ineffective VM capture may make these two types of capture difficult to distinguish from the His bundle near field signal in some patients, particularly when a far field signal 402 is unavailable in the His bundle pacing device. Accordingly, establishing a His bundle capture detection threshold by control circuit 80 of the His bundle pacing device based on a QRS waveform feature when a notification from computer apparatus 240 is received indicating effective His bundle capture is confirmed may improve the performance of His bundle pacing device in detecting effective His bundle capture, even when effective His bundle capture includes capture of nearby ventricular myocardial tissue.

In the examples of FIG. 9, the far field evoked QRS waveform 408 during effective, NSHB capture is narrower than the far field QRS waveform 406 during ineffective, VM capture. When a far field signal 402 is available in the His bundle pacing device, establishing the His bundle capture detection threshold may include establishing a threshold based on a feature of the far field signal, e.g., based on the far field evoked response signal width, area, and/or QRS waveform morphology. A His bundle capture detection threshold established by control circuit 80 based on a far field QRS waveform may increase the reliability of detecting effective His bundle capture by the His bundle pacing device and may be used alone or in combination with a capture detection threshold based on the near field QRS waveform. A threshold value of the QRS width, a threshold value for the QRS area or a waveform template for His bundle capture detection may be established or determined by the His bundle pacing device in conjunction with the generation of electrical dyssynchrony data and His bundle capture notifications by computing apparatus 240 (of FIG. 4). Any of the features of the far field signal 402 and/or near field signal 412 may be determined by the His bundle pacing device in response to receiving a notification that the computing apparatus 240 has detected effective His bundle capture for establishing a His bundle capture detection threshold to be applied to the given feature for His bundle capture monitoring.

Figure 10:
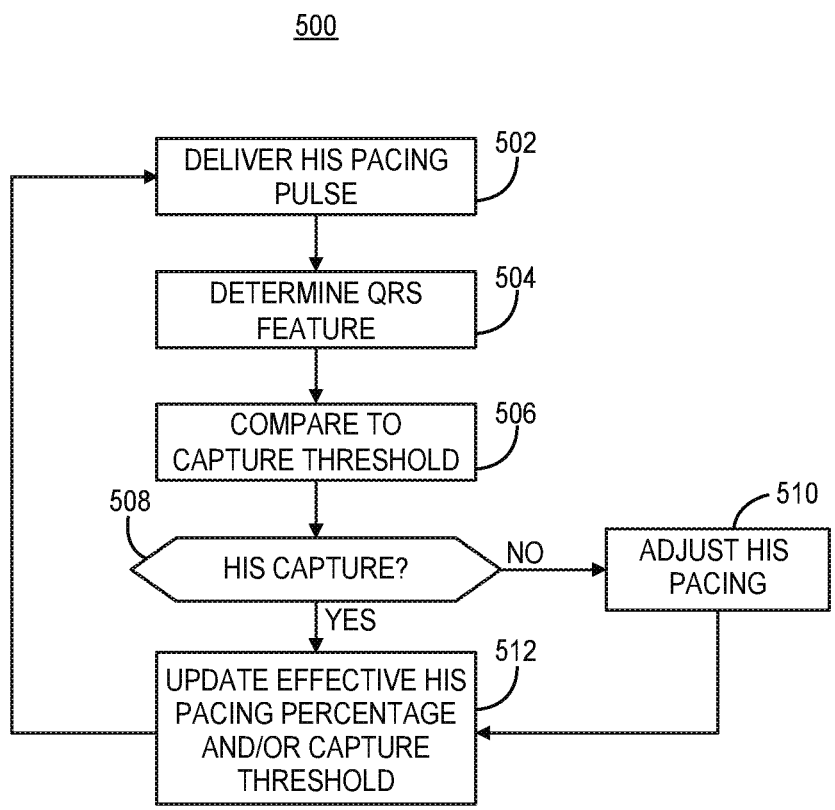
FIG. 10 is a flow chart of a method for monitoring and maintaining His bundle capture by a His bundle pacing device delivering a His bundle pacing therapy according to one example.

FIG. 10 is a flow chart 500 of a method for monitoring and maintaining effective His bundle capture by a His bundle pacing device using an established His bundle capture detection threshold according to one example. In some examples, the process of flow chart 500 may be performed when each His bundle pacing pulse is delivered by the His bundle pacing device. Confirmation of effective His bundle capture by each pacing pulse enables His bundle pacing device to track the overall effectiveness of His bundle pacing, e.g., by determining the percentage of His bundle pacing pulses for which His bundle capture is detected out of all His bundle pacing pulses delivered. In other examples, the process of flow chart 500 may be performed once per day, once per hour, once per minute or other frequency or predetermined capture monitoring schedule. In some examples, the process of flow chart 500 is performed when a triggering event occurs, such as a change in lead impedance is detected or other change is detected that may be correlated to or indicative of a change in His bundle pacing capture threshold.

At block 502, His bundle pacing is delivered according to the programmed pacing therapy protocol and His bundle pacing control parameters. In some examples, the process of flow chart 500 may be performed as part of a pacing capture threshold test in which the His bundle pacing pulse that is delivered at block 502 is one in a sequence of varying pacing amplitude pulses (or varying pulse widths) delivered to determine the lowest pulse amplitude (or lowest pulse width) that results in effective His bundle capture.

At block 504, following the delivery of a His bundle pacing pulse by therapy delivery circuit 84, the cardiac electrical signal feature, specifically a QRS waveform feature, is determined by control circuit 80 from the cardiac electrical signal received from sensing circuit 86 for which the capture detection threshold has been established by control circuit 80 as described in conjunction with FIG. 8. In some examples, multiple QRS waveform features may be determined by control circuit 80 when multiple capture detection thresholds are established. At block 506, control circuit 80 compares the determined cardiac electrical signal feature(s) to the respective, previously established capture detection threshold(s). If His bundle capture detection criteria are met based on the comparison(s) of the determined QRS waveform feature(s) to the established capture detection threshold(s), His bundle capture is detected at block 508 by control circuit 80.

When effective His bundle capture is not detected at block 508 by control circuit 80, e.g., based on one or more determined QRS features not meeting a capture detection threshold, control circuit 80 may signal therapy delivery circuit 84 to adjust the pacing pulse output, e.g., by increasing the pacing pulse amplitude and/or pulse width, at block 510. The next His bundle pacing pulse may be delivered at block 502 according to the increased pulse output (or other adjustment of a His bundle pacing control parameter such as pacing electrode vector), and the process of detecting capture using the previously established capture detection threshold is repeated.

When His bundle capture monitoring includes maintaining a percentage of effective His bundle pacing pulses by control circuit 80, the percentage of pacing pulses for which capture is detected may be updated at block 512 after making the determination of effective His capture (or not) at block 508. The percentage updated at block 512 by control circuit 80 may be determined as the percentage of all delivered His bundle pacing pulses of the His pacing therapy delivered by therapy delivery circuit 84 that resulted in effective His bundle capture detection by control circuit 80 since the therapy was initiated or over a predetermined time interval, e.g., over a 24-hour interval or over one week as examples. If the process of flow chart 500 is being performed by the His bundle pacing device as part of a capture threshold test, the pacing pulse voltage amplitude and/or pulse width corresponding to the effective capture detection ("yes" branch) or ineffective capture detection ("no" branch) at block 508 may be stored in memory 82 at block 512 to enable control circuit 80 to determine the lowest pacing output at which effective His bundle capture was detected based on the His bundle capture threshold.

After updating data relating to His capture monitoring in memory 82 at block 512, control circuit 80 continues the process of flow chart 500 by returning to block 502 to control delivery of the next His bundle pacing pulse (by therapy delivery circuit 84), which may be delivered at an adjusted His pacing output control parameter. In this way, the His bundle pacing device is configured to maintain or promote effective His bundle capture by determining if effective His bundle capture occurs based on the established His capture detection threshold(s) and adjusting a His bundle pacing control parameter in response to effective His bundle capture not being detected in order to restore effective His bundle capture.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device system has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

Illustrative Embodiments

Embodiment 1. A medical device system, comprising:
an electrode apparatus comprising a plurality of external electrodes configured for monitoring a plurality of body surface electrical signals of a patient; and
a computing apparatus comprising processing circuitry and coupled to the electrode apparatus and configured to:
generate cardiac electrical dyssynchrony data from the body surface electrical signals received from the plurality of external electrodes during delivery of His bundle pacing pulses;
identify effective His bundle capture by the His bundle pacing pulses based on the electrical dyssynchrony data, wherein the effective His bundle capture comprises capture of both a left bundle branch and a right bundle branch of a His bundle; and
generate an indication of His bundle capture in response to identifying the effective His bundle capture.

Embodiment 2. The system of embodiment 1, further comprising a His bundle pacing device, the His bundle pacing device comprising:
a sensing circuit configured to sense a cardiac electrical signal;
a therapy delivery circuit configured to deliver the His bundle pacing pulses; and
a control circuit coupled to the sensing circuit and the therapy delivery circuit and configured to:
receive a communication signal corresponding to the indication of the His bundle capture generated by the computing apparatus;
determine a feature of the cardiac electrical signal in response to receiving the communication signal; and
establish a capture detection threshold based on the determined feature of the cardiac electrical signal.

Embodiment 3. The system of embodiment 2, wherein the control circuit is further configured to control the therapy delivery circuit to maintain effective His bundle capture by:
determining the feature of the cardiac electrical signal received from the sensing circuit following a His bundle pacing pulse delivered by the therapy delivery circuit;
comparing the feature to the established capture detection threshold; and
adjusting a pacing control parameter used by the therapy delivery circuit to deliver the His bundle pacing pulses in response to the feature not satisfying the established capture detection threshold.

Embodiment 4. The system of any of embodiments 2 to 3, wherein the computing apparatus is configured to generate the notification by transmitting a wireless signal,
the His bundle pacing device comprising a telemetry circuit configured to receive the wireless signal directly from the computing apparatus.

Embodiment 5. The system of any of embodiments 2 to 4, wherein the control circuit is configured to determine the feature of the cardiac electrical signal by determining at least one of:
a QRS width, a QRS area, a QRS polarity, a QRS morphology and a QRS time delay from a His bundle pacing pulse.

Embodiments 6. The system of any of embodiments 1 to 5, wherein the computing apparatus is further configured to:
generate baseline electrical dyssynchrony data in an absence of His bundle pacing pulses; and
identify His bundle capture by comparing the electrical dyssynchrony data generated during delivery of His bundle pacing pulses to the baseline electrical dyssynchrony data.

Embodiment 7. The system of embodiment 6, wherein the baseline electrical dyssynchrony data is generated during delivery of pacing pulses that capture ventricular myocardium without capturing the His bundle.

Embodiment 8. The system of any of embodiments 1 to 7, wherein the computing apparatus is configured to:
generate electrical dyssynchrony data by:
determining electrical activation times from a plurality of QRS waveforms received from the electrode apparatus, and
determining a metric of the electrical activation times; and
identify the effective His bundle capture by comparing the metric of the electrical activation times to a threshold.

Embodiment 9. The system of any of embodiments 1 to 8, wherein the computing apparatus is further configured to:
generate electrical dyssynchrony data by:
determining a right ventricular metric of electrical activation times from a first plurality of QRS waveforms received from the electrode apparatus corresponding to body surface electrical signals received along a right side of the patient, and
determining a left ventricular metric of electrical activation times from a second plurality of QRS waveforms of the body surface electrical signals received from external electrodes of the electrode apparatus along a left side of the patient; and
identify effective His bundle capture by:
comparing the right ventricular metric and the left ventricular metric to a respective right bundle branch capture threshold and left bundle branch capture threshold; and
identifying effective His bundle capture in response to both of the right ventricular metric and the left ventricular metric meeting the respective right bundle branch capture threshold and left bundle branch capture threshold.

Embodiment 10. The system of any of embodiments 1 to 9, wherein the computer apparatus is further configured to:
discriminate between at least two different types of His bundle capture from among selective His bundle capture, non-selective His bundle capture, ventricular myocardial only capture, right bundle branch capture, and left bundle branch capture based on an analysis of the generated electrical dyssynchrony data; and
generate a notification corresponding to a discriminated type of His bundle capture.

Embodiment 11. The system of any of embodiments 1 to 10, wherein the electrode apparatus comprises an array of electrodes coupled to a substrate configured to circumscribe a torso of the patient.

Embodiment 12. A method performed by a medical device system, comprising:
receiving body surface electrical signals by a computing apparatus from an electrode apparatus comprising a plurality of external electrodes;
generating electrical dyssynchrony data by the computing apparatus from the body surface electrical signals received from the plurality of external electrodes during delivery of His bundle pacing pulses;
identifying, by the computing apparatus, effective His bundle capture based on the electrical dyssynchrony data, wherein the effective His bundle capture comprises capture of both a left bundle branch and a right bundle branch of a His bundle; and
generating an indication of His bundle capture by the computing apparatus in response to identifying the effective His bundle capture.

Embodiment 13. The method of embodiment 12, further comprising:
delivering His bundle pacing pulses by a therapy delivery circuit of a His bundle pacing device;
sensing a cardiac electrical signal by a sensing circuit of the His bundle pacing device;
receiving a communication signal by a telemetry circuit of the His bundle pacing device corresponding to the indication of the His bundle capture generated by the computing apparatus;
determining, by a control circuit of the His bundle pacing device, a feature of the sensed cardiac electrical signal in response to receiving the communication signal; and
establishing a capture detection threshold based on the determined feature of the sensed cardiac electrical signal.

Embodiment 14. The method of embodiment 13, further comprising maintaining His bundle capture by:
determining the feature of the cardiac electrical signal received from the sensing circuit following a His bundle pacing pulse delivered by the therapy delivery circuit;
comparing the feature to the established capture detection threshold; and
adjusting a pacing control parameter used by the therapy delivery circuit to deliver the His bundle pacing pulses in response to the feature not satisfying the established capture detection threshold.

Embodiment 15. The method of any of embodiments 13 to 14, further comprising:
generating the notification by transmitting a wireless signal by the computing apparatus; and
receiving the wireless signal by the His bundle pacing device directly from the computing apparatus.

Embodiment 16. The method of any of embodiments 13-15, wherein determining the feature of the cardiac electrical signal comprises determining at least one of:
a QRS width, a QRS area, a QRS polarity, a QRS morphology and a QRS time delay from a His bundle pacing pulse.

Embodiment 17. The method of any of embodiments 12 to 16, further comprising:
generating baseline electrical dyssynchrony data by the computing apparatus in an absence of His bundle pacing pulses; and
identifying His bundle capture by comparing the electrical dyssynchrony data generated during delivery of His bundle pacing pulses to the baseline electrical dyssynchrony data; and Embodiment 18. The method of embodiment 17, further comprising generating the baseline electrical dyssynchrony data during delivery of pacing pulses that capture ventricular myocardium without capturing the His bundle.

Embodiment 19. The method of any of embodiments 12 to 18, wherein:
generating electrical dyssynchrony data comprises:
determining electrical activation times from a plurality of QRS waveforms received from the electrode apparatus, and
determining a metric of the electrical activation times; and
identifying the effective His bundle capture comprises comparing the metric of the electrical activation times to a threshold.

Embodiment 20. The method of any of embodiments 12 to 19, wherein:
generating electrical dyssynchrony data comprises:
determining a right ventricular metric of electrical activation times from a first plurality of QRS waveforms received from the electrode apparatus corresponding to body surface electrical signals received along a right side of the patient, and
determining a left ventricular metric of electrical activation times from a second plurality of QRS waveforms of the body surface electrical signals received from external electrodes of the electrode apparatus along a left side of the patient; and
identifying effective His bundle capture comprises:
comparing the right ventricular metric and the left ventricular metric to a respective right bundle branch capture threshold and left bundle branch capture threshold; and
identifying effective His bundle capture in response to both of the right ventricular metric and the left ventricular metric meeting the respective right bundle branch capture threshold and left bundle branch capture threshold.

Embodiment 21. The method of any of embodiments 12 to 20, further comprising:
discriminating between at least two different types of His bundle capture from among selective His bundle capture, non-selective His bundle capture, ventricular myocardial only capture, right bundle branch capture, and left bundle branch capture based on an analysis of the generated electrical dyssynchrony data; and
generating a notification corresponding to a discriminated type of His bundle capture.

Embodiment 22. The method of any of embodiments 12 to 21, wherein receiving the body surface electrical signals from the electrode apparatus comprises receiving the body surface electrical signals from an array of the plurality of external electrodes coupled to a substrate configured to circumscribe a torso of the patient.

Embodiment 23. A non-transitory, computer-readable storage medium comprising a set of instructions which, when executed by a processor of a computing apparatus of a medical device system, cause the computing apparatus to:
receive body surface electrical signals from an electrode apparatus comprising a plurality of external electrodes;
generate electrical dyssynchrony data from the body surface electrical signals received from the plurality of external electrodes during delivery of His bundle pacing pulses;
identify effective His bundle capture based on the electrical dyssynchrony data, wherein the effective His bundle capture comprises capture of both a left bundle branch and a right bundle branch of a His bundle; and
generate an indication of His bundle capture in response to identifying the effective His bundle capture.

What is claimed is:

1. A medical device system, comprising:
   an electrode apparatus comprising a plurality of external electrodes configured for monitoring a plurality of body surface electrical signals of a patient;
   a computing apparatus coupled to the electrode apparatus and comprising processing circuitry configured to:
      generate cardiac electrical dyssynchrony data from the body surface electrical signals received from the plurality of external electrodes during delivery of His bundle pacing pulses;
      identify effective His bundle capture by the His bundle pacing pulses based on the electrical dyssynchrony data, wherein the effective His bundle capture comprises capture of both a left bundle branch and a right bundle branch of a His bundle; and
      generate an indication of the effective His bundle capture in response to identifying the effective His bundle capture; and
   a His bundle pacing device, the His bundle pacing device comprising:
      a sensing circuit configured to sense a cardiac electrical signal;
      a therapy delivery circuit configured to deliver the His bundle pacing pulses according to a first pacing output control parameter of a plurality of pacing output control parameters; and
      a control circuit coupled to the sensing circuit and the therapy delivery circuit and configured to:
         receive the indication of the effective His bundle capture generated by the computing apparatus;
         determine confirmed effective His bundle pacing at the first pacing output control parameter associated with the receipt of the indication of the effective His bundle capture;
         determine a feature of the cardiac electrical signal sensed by the sensing circuit during the confirmed effective His bundle pacing at the first pacing output control parameter in response to determining the confirmed effective His bundle capture; and
         establish an effective His bundle capture detection threshold based on the determined feature of the cardiac electrical signal sensed by the sensing circuit during the confirmed effective His bundle pacing.

2. The system of claim 1, wherein the control circuit of the His bundle pacing device is further configured to control the therapy delivery circuit to maintain effective His bundle capture by:
   determining the feature of the cardiac electrical signal received from the sensing circuit following a His bundle pacing pulse delivered by the therapy delivery circuit;
   comparing the feature to the established capture detection threshold; and
   adjusting the first pacing control parameter used by the therapy delivery circuit to deliver the His bundle pacing pulses to a second pacing control parameter of the plurality of pacing control parameters in response to the feature not satisfying the established effective His bundle capture detection threshold.

3. The system of claim 1, wherein the computing apparatus is configured to generate the indication of effective His bundle capture by transmitting a wireless signal,
   the His bundle pacing device comprising a telemetry circuit configured to receive the wireless signal directly from the computing apparatus.

4. The system of claim 1, wherein the control circuit is configured to determine the feature of the cardiac electrical signal by determining at least one of:
   a QRS width, a QRS area, a QRS polarity, a QRS morphology and a QRS time delay from a His bundle pacing pulse.

5. The system of claim 1, wherein the computing apparatus is further configured to:
   generate baseline electrical dyssynchrony data in an absence of His bundle pacing pulses; and
   identify His bundle capture by comparing the electrical dyssynchrony data generated during delivery of His bundle pacing pulses to the baseline electrical dyssynchrony data.

6. The system of claim 5, wherein the baseline electrical dyssynchrony data is generated during delivery of pacing pulses that capture ventricular myocardium without capturing the His bundle.

7. The system of claim 1, wherein the computing apparatus is configured to:
   generate electrical dyssynchrony data by:
      determining electrical activation times from a plurality of QRS waveforms received from the electrode apparatus, and
      determining a metric of the electrical activation times; and
   identify the effective His bundle capture by comparing the metric of the electrical activation times to a threshold.

8. The system of claim 1, wherein the computing apparatus is further configured to:
   generate electrical dyssynchrony data by:
      determining a right ventricular metric of electrical activation times from a first plurality of QRS waveforms received from the electrode apparatus corresponding to body surface electrical signals received along a right side of the patient, and
      determining a left ventricular metric of electrical activation times from a second plurality of QRS waveforms of the body surface electrical signals received from external electrodes of the electrode apparatus along a left side of the patient; and
   identify effective His bundle capture by:
      comparing the right ventricular metric and the left ventricular metric to a respective right bundle branch capture threshold and left bundle branch capture threshold; and
      identifying effective His bundle capture in response to both of the right ventricular metric meeting the respective right bundle branch capture threshold and the left ventricular metric meeting the left bundle branch capture threshold.

9. The system of claim 1, wherein the computer apparatus is further configured to:
   discriminate between at least two different types of His bundle capture from among selective His bundle capture, non-selective His bundle capture, ventricular myocardial only capture, right bundle branch capture, and left bundle branch capture based on an analysis of the generated electrical dyssynchrony data; and
   generate a notification corresponding to a discriminated type of His bundle capture.

10. The system of claim 1, wherein the electrode apparatus comprises an array of electrodes coupled to a substrate configured to circumscribe a torso of the patient.

11. A method performed by a medical device system, comprising:
receiving body surface electrical signals by a computing apparatus from an electrode apparatus comprising a plurality of external electrodes;
generating electrical dyssynchrony data by the computing apparatus from the body surface electrical signals received from the plurality of external electrodes during delivery of His bundle pacing pulses;
identifying, by the computing apparatus, effective His bundle capture based on the electrical dyssynchrony data, wherein the effective His bundle capture comprises capture of both a left bundle branch and a right bundle branch of a His bundle; and
generating an indication of the effective His bundle capture by the computing apparatus in response to identifying the effective His bundle capture;
delivering the His bundle pacing pulses by a His bundle pacing device according to a first pacing output control parameter of a plurality of pacing output control parameters;
sensing a cardiac electrical signal by the His bundle pacing device;
receiving by the His bundle pacing device the indication of the effective His bundle capture generated by the computing apparatus;
determining by the His bundle pacing device confirmed effective His bundle pacing at the first pacing output control parameter associated with the receipt of the indication of the effective His bundle capture;
determining by the His bundle pacing device a feature of the cardiac electrical signal sensed during the confirmed effective His bundle pacing at the first pacing output control parameter in response to determining the confirmed effective His bundle capture; and
establishing by the His bundle pacing device an effective His bundle capture detection threshold based on the determined feature of the cardiac electrical signal sensed during the confirmed effective His bundle pacing.

12. The method of claim 11, further comprising maintaining His bundle capture by:
determining the feature of the cardiac electrical signal received following a His bundle pacing pulse delivered by the His bundle pacing device;
comparing the feature to the established effective His bundle capture detection threshold; and
adjusting the first pacing output control parameter used to deliver the His bundle pacing pulses to a second pacing output control parameter of the plurality of pacing output control parameters in response to the feature not satisfying the established effective His bundle capture detection threshold.

13. The method of claim 11, further comprising:
generating the indication of effective His bundle capture by transmitting a wireless signal by the computing apparatus; and
receiving the wireless signal by the His bundle pacing device directly from the computing apparatus.

14. The method of claim 11, wherein determining the feature of the cardiac electrical signal comprises determining at least one of:
a QRS width, a QRS area, a QRS polarity, a QRS morphology and a QRS time delay from a His bundle pacing pulse.

15. The method of claim 11, further comprising:
generating baseline electrical dyssynchrony data by the computing apparatus in an absence of His bundle pacing pulses; and
identifying His bundle capture by comparing the electrical dyssynchrony data generated during delivery of His bundle pacing pulses to the baseline electrical dyssynchrony data.

16. The method of claim 15, further comprising generating the baseline electrical dyssynchrony data during delivery of pacing pulses that capture ventricular myocardium without capturing the His bundle.

17. The method of claim 11, wherein:
generating electrical dyssynchrony data comprises:
determining electrical activation times from a plurality of QRS waveforms received from the electrode apparatus, and
determining a metric of the electrical activation times; and
identifying the effective His bundle capture comprises comparing the metric of the electrical activation times to a threshold.

18. The method of claim 11, wherein:
generating electrical dyssynchrony data comprises:
determining a right ventricular metric of electrical activation times from a first plurality of QRS waveforms received from the electrode apparatus corresponding to body surface electrical signals received along a right side of the patient, and
determining a left ventricular metric of electrical activation times from a second plurality of QRS waveforms of the body surface electrical signals received from external electrodes of the electrode apparatus along a left side of the patient; and
identifying effective His bundle capture comprises:
comparing the right ventricular metric and the left ventricular metric to a respective right bundle branch capture threshold and left bundle branch capture threshold; and
identifying effective His bundle capture in response to both of the right ventricular metric meeting the right bundle branch capture threshold and the left ventricular metric meeting the left bundle branch capture threshold.

19. The method of claim 11, further comprising:
discriminating between at least two different types of His bundle capture from among selective His bundle capture, non-selective His bundle capture, ventricular myocardial only capture, right bundle branch capture, and left bundle branch capture based on an analysis of the generated electrical dyssynchrony data; and
generating a notification corresponding to a discriminated type of His bundle capture.

20. The method of claim 11, wherein receiving the body surface electrical signals from the electrode apparatus comprises receiving the body surface electrical signals from an array of the plurality of external electrodes coupled to a substrate configured to circumscribe a torso of the patient.

21. A non-transitory, computer-readable storage medium comprising a set of instructions which, when executed by a processor of a medical device system comprising a His bundle pacing device, cause the medical device system to:
receive body surface electrical signals from an electrode apparatus comprising a plurality of external electrodes;
generate electrical dyssynchrony data from the body surface electrical signals received from the plurality of external electrodes during delivery of His bundle pacing pulses;

identify effective His bundle capture based on the electrical dyssynchrony data, wherein the effective His bundle capture comprises capture of both a left bundle branch and a right bundle branch of a His bundle;
generate an indication of the effective His bundle capture in response to identifying the effective His bundle capture;
deliver the His bundle pacing pulses by the His bundle pacing device according to a first pacing output control parameter of a plurality of pacing output control parameters;
sense a cardiac electrical signal by the His bundle pacing device;
receive by the His bundle pacing device the indication of the effective His bundle capture determine by the His bundle pacing device confirmed effective His bundle pacing at the first pacing output control parameter associated with the receipt of the indication of the effective His bundle capture;
determine by the His bundle pacing device confirmed effective His bundle pacing at the first pacing output control parameter associated with the receipt of the indication of the effective His bundle capture;
determine by the His bundle pacing device a feature of the cardiac electrical signal sensed during the confirmed effective His bundle pacing at the first pacing output control parameter in response to determining the confirmed effective His bundle capture; and
establish by the His bundle pacing device an effective His bundle capture detection threshold based on the determined feature of the cardiac electrical signal sensed during the confirmed effective His bundle pacing.

22. An implantable medical device, comprising:
a sensing circuit configured to sense a cardiac electrical signal;
a therapy delivery circuit configured to deliver His bundle pacing pulses according to a first pacing output control parameter; and
a control circuit coupled to the sensing circuit and the therapy delivery circuit and configured to:
receive an indication of effective His bundle capture;
determine confirmed effective His bundle pacing at the first pacing output control parameter associated with the receipt of the indication of the effective His bundle capture;
determine a feature of the cardiac electrical signal sensed by the sensing circuit during the confirmed effective His bundle pacing at the first pacing output control parameter in response to determining the confirmed effective His bundle capture; and
establish an effective His bundle capture detection threshold based on the determined feature of the cardiac electrical signal sensed by the sensing circuit during the confirmed effective His bundle pacing.

23. The implantable medical device of claim 22, wherein the control circuit is further configured to control the therapy delivery circuit to maintain effective His bundle capture by:
determining the feature of the cardiac electrical signal received from the sensing circuit following a His bundle pacing pulse delivered by the therapy delivery circuit;
comparing the feature to the established effective His bundle capture detection threshold; and
adjusting the first pacing control parameter used by the therapy delivery circuit to deliver the His bundle pacing pulses to a second pacing control parameter of a plurality of pacing control parameters in response to the feature not satisfying the established effective His bundle capture detection threshold.

24. The implantable medical device of claim 22, further comprising:
a telemetry circuit configured to receive the indication of effective His bundle capture transmitted by a computing apparatus;
wherein the control circuit is further configured to receive the indication of effective His bundle capture via the telemetry circuit.

25. The implantable medical device of claim 22, wherein the control circuit is configured to determine the feature of the cardiac electrical signal by determining at least one of:
a QRS width, a QRS area, a QRS polarity, a QRS morphology template and a QRS time delay from a His bundle pacing pulse.

26. The implantable medical device of claim 22, wherein the control circuit is further configured to:
control the therapy delivery circuit to deliver the His bundle pacing pulses at a second pacing pulse output control parameter;
determine that the indication of effective His bundle capture is not received during His bundle pacing at the second pacing pulse output control parameter; and
control the therapy delivery circuit to adjust the second pacing pulse output control parameter to the first pacing pulse output control parameter in response to not receiving the indication of effective His bundle capture during His bundle pacing at the second pacing pulse output control parameter.

27. The implantable medical device of claim 22, wherein the control circuit is further configured to:
determine a baseline QRS feature of the cardiac electrical signal during His bundle non-capture; and
establish the effective His bundle capture detection threshold by setting the His bundle capture detection threshold to a value between the baseline QRS feature value and the determined feature of the cardiac electrical signal sensed by the sensing circuit during the confirmed effective His bundle pacing.

* * * * *